United States Patent
Pitterna et al.

(10) Patent No.: US 8,110,684 B2
(45) Date of Patent: Feb. 7, 2012

(54) DIAZA-SPIRO [4.5] DECANES USEFUL AS PESTICIDES

(75) Inventors: Thomas Pitterna, Basel (GB); Jerome Cassayre, Basel (CH); Louis-Pierre Molleyres, Basel (CH); Peter Maienfisch, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 735 days.

(21) Appl. No.: 12/161,823

(22) PCT Filed: Jan. 19, 2007

(86) PCT No.: PCT/IB2007/000176
§ 371 (c)(1),
(2), (4) Date: Jul. 23, 2008

(87) PCT Pub. No.: WO2007/085945
PCT Pub. Date: Aug. 2, 2007

(65) Prior Publication Data

US 2010/0227862 A1   Sep. 9, 2010

(30) Foreign Application Priority Data

Jan. 24, 2006  (GB) .................................. 0601402.1

(51) Int. Cl.
C07D 217/00 (2006.01)
A61K 31/44 (2006.01)
(52) U.S. Cl. .......................................... 546/16; 514/278
(58) Field of Classification Search .................... None
See application file for complete search history.

(56) References Cited

U.S. PATENT DOCUMENTS 6,482,829 B2 * 11/2002 Galley et al. .................. 514/278

FOREIGN PATENT DOCUMENTS

| WO | 0194346 | 12/2001 |
| WO | 03106457 | 12/2003 |
| WO | 2005058897 | 6/2005 |

OTHER PUBLICATIONS

Silverman, R. "The Organic Chemistry of Drug Design and Drug Action," 2004, Elsevier, pp. 29-32.*

* cited by examiner

*Primary Examiner* — Janet L. Andres
*Assistant Examiner* — Heidi Reese
(74) *Attorney, Agent, or Firm* — William A. Teoli, Jr.

(57) ABSTRACT

A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) wherein Y is a single bond, C=O, C=S or $S(O)_m$ where m is 0, 1 or 2; and $R^1$, $R^3$, $R^2$ and $R^8$ are defined organic, groups, p is 0, 1, 2, 3 or 4 or salts or N-oxides thereof; novel compounds and composition's containing them are also provided.

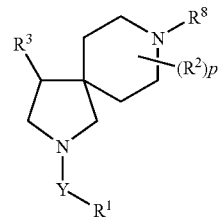

(I)

20 Claims, No Drawings

DIAZA-SPIRO [4.5] DECANES USEFUL AS PESTICIDES

This application is a 371 of International Application No. PCT/IB2007/000176 filed Jan. 19, 2007, which claims priority to GB 0601402.1 filed Jan. 24, 2006, the contents of which are incorporated herein by reference.

The present invention relates to piperidine derivatives, to processes for preparing them, to insecticidal, acaricidal, molluscicidal and nematicidal compositions comprising them and to methods of using them to combat and control insect, acarine, mollusc and nematode pests.

Diaza-spiro[4.5]decane derivatives with pharmaceutical properties are disclosed in for example in WO01/94346, WO05/007656, WO05/023809 and WO05/040167.

It has now surprisingly been found that certain diaza-spiro [4.5]decanes have insecticidal properties.

The present invention therefore provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

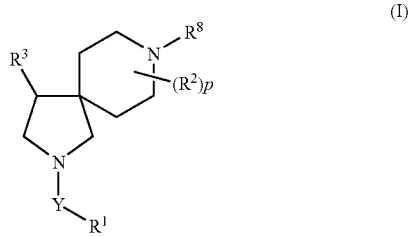

Y is a single bond, C=O, C=S or $S(O)_m$, where m is 0, 1 or 2;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$NR^{17}R^{18}$ or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^3$ is optionally substituted aryl or optionally substituted heteroaryl;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

Each $R^2$ is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further hetero atoms selected from O, N or S and which may be optionally substituted by one or two $C_{1-6}$ alkyl groups, or two $R^2$ groups attached to the same carbon atom are =O, =S =$NR^5$, =$CR^6R^7$ where $R^5$, $R^6$ and $R^7$ are independently H or optionally substituted alkyl; p is 0, 1, 2, 3 or 4 or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably $C_1$-$C_6$ and most preferably $C_1$-$C_4$ alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl ($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$) alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri ($C_{1-4}$)alkylsilyl,aryldi ($C_{1-4}$)alkylsilyl,($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)

aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkenylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-($C_{1-6}$) alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkyl-silyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio $C_{3-7}$ cycloalkylthio (where the cycloalkyl group is optionally substituted with $C_{1-6}$ alkyl or halogen), tri($C_{1-4}$)-alkylsilyl($C_{1-6}$)alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$)-alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$) alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), ($C_{1-6}$)alkyloxycarbonylamino ($C_{1-6}$)alkyloxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the awl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di($C_{1-6}$)alkylaminocarbonyl amino, arylaminocarbonyl amino where the awl group is substituted by $C_{1-6}$ alkyl or halogen), aryl-N—($C_{1-6}$)alkylamino-carbonylamino where the aryl group is substituted by $C_{1-6}$ alkyl or halogen), $C_{1-6}$ alkylaminocarbonyl-N—($C_{1-6}$) alkyl amino, di($C_{1-6}$)alkylaminocarbonyl-N—($C_{1-6}$)alkyl amino, arylaminocarbonyl-N—($C_{1-6}$)alkyl amino where the aryl group is substituted by $C_{1-6}$ alkyl or halogen) and aryl-N—($C_{1-6}$)alkylaminocarbonyl-N—($C_{1-6}$)alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{25}R^{26}N$ or $R^{27}R^{28}NC(O)$; wherein $R^{25}$, $R^{26}$, $R^{27}$ and $R^{28}$ are, independently, hydrogen or $C_{1-6}$ alkyl. Further preferred substituents are aryl and heteroaryl groups.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$alkoxy, $C_{1-10}$ alkylthio, $C_{1-10}$ alkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri-($C_{1-4}$)alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

Preferred groups for Y, $R^1$, $R^2$, $R^3$ and $R^8$ in any combination thereof are set out below.

Preferably Y is a single bond, C=O or C=S.

More preferably Y is a single bond or C=O.

Most preferably Y is C=O.

Preferably $R^1$ is hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl), phenyl($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino)).

More preferably $R^1$ is $C_{1-6}$ alkyl, $C_{1-6}$ haloalkyl, $C_{1-6}$ alkoxy($C_{1-6}$)alkyl, heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, $C_{2-6}$ alkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl or $C_{1-6}$ haloalkyl, $C_{1-6}$ alkoxy($C_{1-6}$)alkyl, $C_{2-6}$ alkylcarbonyl, phenylcarbonyl, (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen) or heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen).

Even more preferably $R^1$ is $C_{1-6}$ alkyl, $C_{1-6}$ haloalkyl, heteroaryl($C_{1-3}$)alkyl (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring), heteroaryl (optionally substituted by halo, cyano, $C_{1-6}$ alkyl, $C_{1-6}$ haloalkyl and where the heteroaryl group is a pyridine, pyrimidine, 2,1,3-benzoxadiazole, pyrazine or pyridazine ring), $C_{1-6}$ alkoxy, $C_{1-6}$ alkoxy($C_{1-6}$)alkyl, $C_{1-6}$ alkylamino, alkyoxy($C_{1-6}$)alkylamino or heteroaryl($C_{1-3}$)alkylamino (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring).

Most preferably $R^1$ is pyridyl (optionally substituted by halo, $C_{1-3}$ alkyl or $C_{1-3}$ haloalkyl) especially halo-substituted pyridyl.

It is preferred that $R^3$ is a 6-membered aromatic ring or is 5 or 6 membered heteroaromatic ring wherein the ring members are each independently CH, S, N, $NR^4$, O, or $CR^4$ where $R^4$ is as defined below provided that there are no more than one O or S atoms present in the ring.

More preferably $R^3$ is a benzene, pyridine, pyrimidine, pyrazine, pyridazine, triazine, pyrrole, imidazole, quinoline, isoquinoline, thiophene, pyrazole, oxazole, thiazole, isoxazole, isothiazole, [1,2,3]triazole, [1,2,3]oxadiazole or [1,2,3]thiadiazole ring substituted by 0, 1, 2 or 3 $R^4$ groups.

Even more preferably $R^3$ is a benzene, pyridine, pyrimidine, pyrazine, thiophene or pyrazole ring substituted by 0, 1, 2 or 3 $R^4$ groups.

Most preferably $R^3$ is a benzene ring by 0, 1, 2 or 3 $R^4$ groups.

Each $R^4$ is independently halogen, cyano, $C_{1-8}$ alkyl, $C_{1-8}$ haloalkyl, $C_{1-6}$ cyanoalkyl, $C_{1-6}$ alkoxy($C_{1-6}$)alkyl, $C_{3-7}$ cycloalkyl($C_{1-6}$)alkyl, $C_{5-6}$ cycloalkenyl($C_{1-6}$)alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl-($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl ($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl ($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, trimethylsilyl($C_{2-6}$)alkynyl, aminocarbonyl($C_{2-6}$)alkynyl, $C_{1-6}$ alkylaminocarbonyl($C_{2-6}$)alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the atoms to which they are attached form a 4, 5, 6 or 7 membered carbocylic, heteroaromatic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^9R^{10}N$ where $R^9$ and $R^{10}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^9$ and $R^{10}$ together with the N atom to which they are attached form a five, six or seven-membered heterocyclic ring which may contain one or two further heteroatoms selected from O, N or S and which may be optionally substituted by one or two $C_{1-6}$ alkyl groups.

Preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$) alkyl, $C_{2-6}$ alkynyl, trimethylsilyl($C_{2-6}$)alkynyl, $C_{1-6}$ alkoxycarbonyl, $C_{3-7}$ cycloalkyl, $C_{1-3}$ alkyl($C_{3-7}$) cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), di($C_{1-8}$)alkylamino, or 2 adjacent groups $R^4$ together with the atoms to which they are attached form a 4, 5, 6 or 7 membered carbocyclic, heteroaromatic or heterocyclic ring which may be optionally substituted by halogen.

More preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$) alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di($C_{1-8}$)alkylamino or 2 adjacent groups $R^4$ together with the atoms to which they are attached form a 4, 5, 6 or 7 membered carbocyclic, heteroaromatic or heterocyclic ring which may be optionally substituted by halogen.

Yet more preferably each $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl.

Most preferably each $R^4$ is independently fluoro, chloro, bromo, $C_{1-4}$ alkyl or $C_{1-4}$ haloalkyl.

Preferably $R^8$ is $C_{1-10}$ alkyl, $C_{1-10}$ haloalkyl, aryl($C_{1-6}$) alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenyl-carbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or —C($R^{51}$)($R^{52}$)—[$CR^{53}$=$CR^{54}$]z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

More preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, haloalkyl, $C_{1-4}$ haloalkoxy, CN, $NO_2$, aryl, heteroaryl, amino or dialkylamino), phenyl($C_{2-6}$) alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{2-6}$)alkenyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or —C($R^{51}$)($R^{52}$)—{$CR^{53}$=$CR^{54}$}z-$R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

Most preferably $R^8$ is —C($R^{51}$)($R^{52}$)—[$CR^{53}$=$CR^{54}$]z-$R^{55}$ where z is 1 or 2, preferably 1, $R^{51}$ and $R^{52}$ are each independently H or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

$R^{51}$ and $R^{52}$ are preferably hydrogen.

$R^{53}$ and $R^{54}$ are preferably hydrogen or halogen, especially hydrogen.

$R^{55}$ is preferably phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

Preferably each $R^2$ is independently halo, cyano, $C_{1-3}$ alkyl, hydroxy or two $R^2$ groups together with the carbon atom to which they are attached form =O, =$NR^5$, =$CR^6R^7$ where $R^8$, $R^6$ and $R^7$ are independently H or optionally substituted alkyl, and p is 0, 1 or 2.

More preferably each $R^2$ is independently fluoro, methyl, hydroxy or two $R^2$ groups together with the carbon atom to which they are attached form a carbonyl group and p is 0, 1 or 2.

Most preferably p is 0.

Certain compounds of formula (I) are novel and as such form a further aspect of the invention. One group of novel compounds are compounds of formula I'

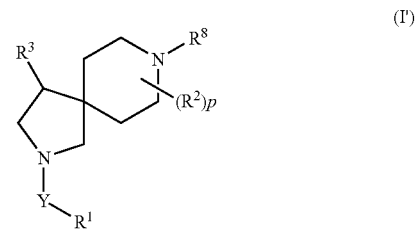

(I')

wherein $R^1$, $R^2$, $R^3$, $R^8$, Y and p are as defined in relation to formula I provided that $R^3$ is other than unsubstituted phenyl or salts or N-oxides thereof.

Another group of novel compounds of formula (I) are those of formula I'"

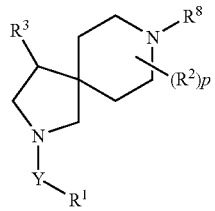

wherein $R^1$, $R^2$, $R^3$, Y and p are as defined in relation to formula I and $R^8$ is —$C(R^{51})(R^{52})$—$[CR^{53}=CR^{54}]z$-$R^{55}$ where z is 1 or 2, preferably 1, $R^{51}$ and $R^{52}$ are each independently H or $C_{1-2}$ alkyl, $R^{53}$ and $R^{54}$ are each independently H, halogen, $C_{1-2}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or salts or N-oxides thereof.

The compounds in Tables I to XXV below illustrate the compounds of the invention.

Table I provides 913 compounds of formula Ia

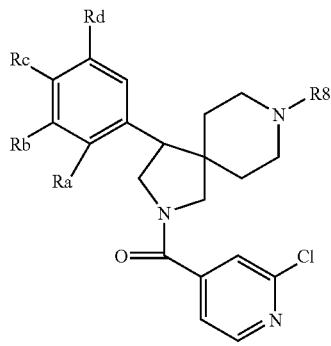

wherein the values of $R^8$, $R^a$, $R^b$, $R^c$ and $R^d$ are given in Table 1.

TABLE 1

| Compound No | $R^8$ | $R^a$ | $R^b$ | $R^c$ | $R^d$ |
|---|---|---|---|---|---|
| I-1 | 4-chlorobenzyl | H | H | H | H |
| I-2 | Cinnamyl | H | H | H | H |
| I-3 | 4-chlorocinnamyl | H | H | H | H |
| I-4 | 4-fluorocinnamyl | H | H | H | H |
| I-5 | 4-bromocinnamyl | H | H | H | H |
| I-6 | 4-trifluoromethylcinnamyl | H | H | H | H |
| I-7 | 4-trifluoromethoxycinnamyl | H | H | H | H |
| I-8 | 4-pentafluoroethoxycinnamyl | H | H | H | H |
| I-9 | 4-methoxycinnamyl | H | H | H | H |
| I-10 | 4-ethoxycinnamyl | H | H | H | H |
| I-11 | 4-cyanocinnamyl | H | H | H | H |
| I-12 | 3-(6-chloro-pyridin-3-yl)-allyl | H | H | H | H |
| I-13 | 3-(4-chlorophenyl)-but-2-enyl | H | H | H | H |
| I-14 | 3-(4-chlorophenyl)-3-fluoro-allyl | H | H | H | H |
| I-15 | 3-chloro-4-fluoro-cinnamyl | H | H | H | H |
| I-16 | 3,5-dichloro-cinnamyl | H | H | H | H |
| I-17 | 5-phenyl-penta-2,4-dienyl | H | H | H | H |
| I-18 | 4-isopropyloxycarbonylamino-cinnamyl | H | H | H | H |
| I-19 | 3-naphthalen-2-yl-allyl | H | H | H | H |
| I-20 | 3-(5-trifluoromethyl-pyridin-2-yl)-allyl | H | H | H | H |
| I-21 | 3-(5-chloro-pyridin-2-yl)-allyl | H | H | H | H |
| I-22 | 3-pyridin-4-yl-allyl | H | H | H | H |
| I-23 | 3-(2-Chloro-pyridin-4-yl)-allyl | H | H | H | H |
| I-24 | 4-chlorobenzyl | H | F | H | H |
| I-25 | Cinnamyl | H | F | H | H |
| I-26 | 4-chlorocinnamyl | H | F | H | H |
| I-27 | 4-fluorocinnamyl | H | F | H | H |
| I-28 | 4-bromocinnamyl | H | F | H | H |
| I-29 | 4-trifluoromethylcinnamyl | H | F | H | H |
| I-30 | 4-trifluoromethoxycinnamyl | H | F | H | H |
| I-31 | 4-pentafluoroethoxycinnamyl | H | F | H | H |
| I-32 | 4-methoxycinnamyl | H | F | H | H |
| I-33 | 4-ethoxycinnamyl | H | F | H | H |
| I-34 | 4-cyanocinnamyl | H | F | H | H |
| I-35 | 3-(6-chloro-pyridin-3-yl)-allyl | H | F | H | H |
| I-36 | 3-(4-chlorophenyl)-but-2-enyl | H | F | H | H |
| I-37 | 3-(4-chlorophenyl)-3-fluoro-allyl | H | F | H | H |
| I-38 | 3-chloro-4-fluoro-cinnamyl | H | F | H | H |
| I-39 | 3,5-dichloro-cinnamyl | H | F | H | H |
| I-40 | 5-phenyl-penta-2,4-dienyl | H | F | H | H |
| I-41 | 4-isopropyloxycarbonylamino-cinnamyl | H | F | H | H |
| I-42 | 3-naphthalen-2-yl-allyl | H | F | H | H |
| I-43 | 3-(5-trifluoromethyl-pyridin-2-yl)-allyl | H | F | H | H |
| I-44 | 3-(5-chloro-pyridin-2-yl)-allyl | H | F | H | H |
| I-45 | 3-pyridin-4-yl-allyl | H | F | H | H |
| I-46 | 3-(2-Chloro-pyridin-4-yl)-allyl | H | F | H | H |
| I-47 | 4-chlorobenzyl | H | Cl | H | H |
| I-48 | Cinnamyl | H | Cl | H | H |
| I-49 | 4-chlorocinnamyl | H | Cl | H | H |
| I-50 | 4-fluorocinnamyl | H | Cl | H | H |
| I-51 | 4-bromocinnamyl | H | Cl | H | H |
| I-52 | 4-trifluoromethylcinnamyl | H | Cl | H | H |
| I-53 | 4-trifluoromethoxycinnamyl | H | Cl | H | H |
| I-54 | 4-pentafluoroethoxycinnamyl | H | Cl | H | H |
| I-55 | 4-methoxycinnainyl | H | Cl | H | H |
| I-56 | 4-ethoxycinnamyl | H | Cl | H | H |
| I-57 | 4-cyanocinnamyl | H | Cl | H | H |
| I-58 | 3-(6-chloro-pyridin-3-yl)-allyl | H | Cl | H | H |
| I-59 | 3-(4-chlorophenyl)-but-2-enyl | H | Cl | H | H |
| I-60 | 3-(4-chlorophenyl)-3-fluoro-allyl | H | Cl | H | H |
| I-61 | 3-chloro-4-fluoro-cinnamyl | H | Cl | H | H |
| I-62 | 3,5-dichloro-cinnamyl | H | Cl | H | H |
| I-63 | 5-phenyl-penta-2,4-dienyl | H | Cl | H | H |
| I-64 | 4-isopropyloxycarbonylamino-cinnamyl | H | Cl | H | H |
| I-65 | 3-naphthalen-2-yl-allyl | H | Cl | H | H |
| I-66 | 3-(5-trifluoromethyl-pyridin-2-yl)-allyl | H | Cl | H | H |
| I-67 | 3-(5-chloro-pyridin-2-yl)-allyl | H | Cl | H | H |
| I-68 | 3-pyridin-4-yl-allyl | H | Cl | H | H |
| I-69 | 3-(2-Chloro-pyridin-4-yl)-allyl | H | Cl | H | H |
| I-70 | 4-chlorobenzyl | H | H | F | H |
| I-71 | Cinnamyl | H | H | F | H |
| I-72 | 4-chlorocinnamyl | H | H | F | H |
| I-73 | 4-fluorocinnamyl | H | H | F | H |
| I-74 | 4-bromocinnamyl | H | H | F | H |
| I-75 | 4-trifluoromethylcinnamyl | H | H | F | H |
| I-76 | 4-trifluoromethoxycinnamyl | H | H | F | H |
| I-77 | 4-pentafluoroethoxycinnamyl | H | H | F | H |
| I-78 | 4-methoxycinnamyl | H | H | F | H |
| I-79 | 4-ethoxycinnamyl | H | H | F | H |
| I-80 | 4-cyanocinnamyl | H | H | F | H |
| I-81 | 3-(6-chloro-pyridin-3-yl)-allyl | H | H | F | H |
| I-82 | 3-(4-chlorophenyl)-but-2-enyl | H | H | F | H |
| I-83 | 3-(4-chlorophenyl)-3-fluoro-allyl | H | H | F | H |
| I-84 | 3-chloro-4-fluoro-cinnamyl | H | H | F | H |
| I-85 | 3,5-dichloro-cinnamyl | H | H | F | H |

TABLE 1-continued

| Compound No | R⁸ | Rᵃ | Rᵇ | Rᶜ | Rᵈ |
|---|---|---|---|---|---|
| I-86 | 5-phenyl-penta-2,4-dienyl | H | H | F | H |
| I-87 | 4-isopropyloxycarbonylamino-cinnamyl | H | H | F | H |
| I-88 | 3-naphthalen-2-yl-allyl | H | H | F | H |
| I-89 | 3-(5-trifluoromethyl-pyridin-2-yl)-allyl | H | H | F | H |
| I-90 | 3-(5-chloro-pyridin-2-yl)-allyl | H | H | F | H |
| I-91 | 3-pyridin-4-yl-allyl | H | H | F | H |
| I-92 | 3-(2-Chloro-pyridin-4-yl)-allyl | H | H | F | H |
| I-93 | 4-chlorobenzyl | H | H | Cl | H |
| I-94 | Cinnamyl | H | H | Cl | H |
| I-95 | 4-chlorocinnamyl | H | H | Cl | H |
| I-96 | 4-fluorocinnamyl | H | H | Cl | H |
| I-97 | 4-bromocinnamyl | H | H | Cl | H |
| I-98 | 4-trifluoromethylcinnamyl | H | H | Cl | H |
| I-99 | 4-trifluoromethoxycinnamyl | H | H | Cl | H |
| I-100 | 4-pentafluoroethoxycinnamyl | H | H | Cl | H |
| I-101 | 4-methoxycinnamyl | H | H | Cl | H |
| I-102 | 4-ethoxycinnamyl | H | H | Cl | H |
| I-103 | 4-cyanocinnamyl | H | H | Cl | H |
| I-104 | 3-(6-chloro-pyridin-3-yl)-allyl | H | H | Cl | H |
| I-105 | 3-(4-chlorophenyl)-but-2-enyl | H | H | Cl | H |
| I-106 | 3-(4-chlorophenyl)-3-fluoro-allyl | H | H | Cl | H |
| I-107 | 3-chloro-4-fluoro-cinnamyl | H | H | Cl | H |
| I-108 | 3,5-dichloro-cinnamyl | H | H | Cl | H |
| I-109 | 5-phenyl-penta-2,4-dienyl | H | H | Cl | H |
| I-110 | 4-isopropyloxycarbonylamino-cinnamyl | H | H | Cl | H |
| I-111 | 3-naphthalen-2-yl-allyl | H | H | Cl | H |
| I-112 | 3-(5-trifluoromethyl-pyridin-2-yl)-allyl | H | H | Cl | H |
| I-113 | 3-(5-chloro-pyridin-2-yl)-allyl | H | H | Cl | H |
| I-114 | 3-pyridin-4-yl-allyl | H | H | Cl | H |
| I-115 | 3-(2-Chloro-pyridin-4-yl)-allyl | H | H | Cl | H |
| I-116 | 4-chlorobenzyl | Cl | Cl | H | H |
| I-117 | Cinnamyl | Cl | Cl | H | H |
| I-118 | 4-chlorocinnamyl | Cl | Cl | H | H |
| I-119 | 4-fluorocinnamyl | Cl | Cl | H | H |
| I-120 | 4-bromocinnamyl | Cl | Cl | H | H |
| I-121 | 4-trifluoromethylcinnamyl | Cl | Cl | H | H |
| I-122 | 4-trifluoromethoxycinnamyl | Cl | Cl | H | H |
| I-123 | 4-pentafluoroethoxycinnamyl | Cl | Cl | H | H |
| I-124 | 4-methoxycinnamyl | Cl | Cl | H | H |
| I-125 | 4-ethoxycinnamyl | Cl | Cl | H | H |
| I-126 | 4-cyanocinnamyl | Cl | Cl | H | H |
| I-127 | 3-(6-chloro-pyridin-3-yl)-allyl | Cl | Cl | H | H |
| I-128 | 3-(4-chlorophenyl)-but-2-enyl | Cl | Cl | H | H |
| I-129 | 3-(4-chlorophenyl)-3-fluoro-allyl | Cl | Cl | H | H |
| I-130 | 3-chloro-4-fluoro-cinnamyl | Cl | Cl | H | H |
| I-131 | 3,5-dichloro-cinnamyl | Cl | Cl | H | H |
| I-132 | 5-phenyl-penta-2,4-dienyl | Cl | Cl | H | H |
| I-133 | 4-isopropyloxycarbonylamino-cinnamyl | Cl | Cl | H | H |
| I-134 | 3-naphthalen-2-yl-allyl | Cl | Cl | H | H |
| I-135 | 3-(5-trifluoromethyl-pyridin-2-yl)-allyl | Cl | Cl | H | H |
| I-136 | 3-(5-chloro-pyridin-2-yl)-allyl | Cl | Cl | H | H |
| I-137 | 3-pyridin-4-yl-allyl | Cl | Cl | H | H |
| I-138 | 3-(2-Chloro-pyridin-4-yl)-allyl | Cl | Cl | H | H |
| I-139 | 4-chlorobenzyl | F | F | H | H |
| I-140 | Cinnamyl | F | F | H | H |
| I-141 | 4-chlorocinnamyl | F | F | H | H |
| I-142 | 4-fluorocinnamyl | F | F | H | H |
| I-143 | 4-bromocinnamyl | F | F | H | H |
| I-144 | 4-trifluoromethylcinnamyl | F | F | H | H |
| I-145 | 4-trifluoromethoxycinnamyl | F | F | H | H |
| I-146 | 4-pentafluoroethoxycinnamyl | F | F | H | H |
| I-147 | 4-methoxycinnamyl | F | F | H | H |
| I-148 | 4-ethoxycinnamyl | F | F | H | H |
| I-149 | 4-cyanocinnamyl | F | F | H | H |
| I-150 | 3-(6-chloro-pyridin-3-yl)-allyl | F | F | H | H |
| I-151 | 3-(4-chlorophenyl)-but-2-enyl | F | F | H | H |
| I-152 | 3-(4-chlorophenyl)-3-fluoro-allyl | F | F | H | H |
| I-153 | 3-chloro-4-fluoro-cinnamyl | F | F | H | H |
| I-154 | 3,5-dichloro-cinnamyl | F | F | H | H |
| I-155 | 5-phenyl-penta-2,4-dienyl | F | F | H | H |
| I-156 | 4-isopropyloxycarbonylamino-cinnamyl | F | F | H | H |
| I-157 | 3-naphthalen-2-yl-allyl | F | F | H | H |
| I-158 | 3-(5-trifluoromethyl-pyridin-2-yl)-allyl | F | F | H | H |
| I-159 | 3-(5-chloro-pyridin-2-yl)-allyl | F | F | H | H |
| I-160 | 3-pyridin-4-yl-allyl | F | F | H | H |
| I-161 | 3-(2-Chloro-pyridin-4-yl)-allyl | F | F | H | H |
| I-162 | 4-chlorobenzyl | F | H | F | H |
| I-163 | Cinnamyl | F | H | F | H |
| I-164 | 4-chlorocinnamyl | F | H | F | H |
| I-165 | 4-fluorocinnamyl | F | H | F | H |
| I-166 | 4-bromocinnamyl | F | H | F | H |
| I-167 | 4-trifluoromethylcinnamyl | F | H | F | H |
| I-168 | 4-trifluoromethoxycinnamyl | F | H | F | H |
| I-169 | 4-pentafluoroethoxycinnamyl | F | H | F | H |
| I-170 | 4-methoxycinnamyl | F | H | F | H |
| I-171 | 4-ethoxycinnamyl | F | H | F | H |
| I-172 | 4-cyanocinnamyl | F | H | F | H |
| I-173 | 3-(6-chloro-pyridin-3-yl)-allyl | F | H | F | H |
| I-174 | 3-(4-chlorophenyl)-but-2-enyl | F | H | F | H |
| I-175 | 3-(4-chlorophenyl)-3-fluoro-allyl | F | H | F | H |
| I-176 | 3-chloro-4-fluoro-cinnamyl | F | H | F | H |
| I-177 | 3,5-dichloro-cinnamyl | F | H | F | H |
| I-178 | 5-phenyl-penta-2,4-dienyl | F | H | F | H |
| I-179 | 4-isopropyloxycarbonylamino-cinnamyl | F | H | F | H |
| I-180 | 3-naphthalen-2-yl-allyl | F | H | F | H |
| I-181 | 3-(5-trifluoromethyl-pyridin-2-yl)-allyl | F | H | F | H |
| I-182 | 3-(5-chloro-pyridin-2-yl)-allyl | F | H | F | H |
| I-183 | 3-pyridin-4-yl-allyl | F | H | F | H |
| I-184 | 3-(2-Chloro-pyridin-4-yl)-allyl | F | H | F | H |
| I-185 | 4-chlorobenzyl | F | H | H | F |
| I-186 | Cinnamyl | F | H | H | F |
| I-187 | 4-chlorocinnamyl | F | H | H | F |
| I-188 | 4-fluorocinnamyl | F | H | H | F |
| I-189 | 4-bromocinnamyl | F | H | H | F |
| I-190 | 4-trifluoromethylcinnamyl | F | H | H | F |
| I-191 | 4-trifluoromethoxycinnamyl | F | H | H | F |
| I-192 | 4-pentafluoroethoxycinnamyl | F | H | H | F |
| I-193 | 4-methoxycinnamyl | F | H | H | F |
| I-194 | 4-ethoxycinnamyl | F | H | H | F |
| I-195 | 4-cyanocinnamyl | F | H | H | F |
| I-196 | 3-(6-chloro-pyridin-3-yl)-allyl | F | H | H | F |
| I-197 | 3-(4-chlorophenyl)-but-2-enyl | F | H | H | F |
| I-198 | 3-(4-chlorophenyl)-3-fluoro-allyl | F | H | H | F |
| I-199 | 3-chloro-4-fluoro-cinnamyl | F | H | H | F |
| I-200 | 3,5-dichloro-cinnamyl | F | H | H | F |
| I-201 | 5-phenyl-penta-2,4-dienyl | F | H | H | F |
| I-202 | 4-isopropyloxycarbonylamino-cinnamyl | F | H | H | F |
| I-203 | 3-naphthalen-2-yl-allyl | F | H | H | F |
| I-204 | 3-(5-trifluoromethyl-pyridin-2-yl)-allyl | F | H | H | F |
| I-205 | 3-(5-chloro-pyridin-2-yl)-allyl | F | H | H | F |
| I-206 | 3-pyridin-4-yl-allyl | F | H | H | F |
| I-207 | 3-(2-Chloro-pyridin-4-yl)-allyl | F | H | H | F |
| I-208 | 4-chlorobenzyl | Cl | H | Cl | H |
| I-209 | Cinnamyl | Cl | H | Cl | H |
| I-210 | 4-chlorocinnamyl | Cl | H | Cl | H |
| I-211 | 4-fluorocinnamyl | Cl | H | Cl | H |
| I-212 | 4-bromocinnamyl | Cl | H | Cl | H |
| I-213 | 4-trifluoromethylcinnamyl | Cl | H | Cl | H |
| I-214 | 4-trifluoromethoxycinnamyl | Cl | H | Cl | H |
| I-215 | 4-pentafluoroethoxycinnamyl | Cl | H | Cl | H |
| I-216 | 4-methoxycinnamyl | Cl | H | Cl | H |
| I-217 | 4-ethoxycinnamyl | Cl | H | Cl | H |
| I-218 | 4-cyanocinnamyl | Cl | H | Cl | H |
| I-219 | 3-(6-chloro-pyridin-3-yl)-allyl | Cl | H | Cl | H |
| I-220 | 3-(4-chlorophenyl)-but-2-enyl | Cl | H | Cl | H |
| I-221 | 3-(4-chlorophenyl)-3-fluoro-allyl | Cl | H | Cl | H |

TABLE 1-continued

| Compound No | R⁸ | Rᵃ | Rᵇ | Rᶜ | Rᵈ |
|---|---|---|---|---|---|
| I-222 | 3-chloro-4-fluoro-cinnamyl | Cl | H | Cl | H |
| I-223 | 3,5-dichloro-cinnamyl | Cl | H | Cl | H |
| I-224 | 5-phenyl-penta-2,4-dienyl | Cl | H | Cl | H |
| I-225 | 4-isopropyloxycarbonylamino-cinnamyl | Cl | H | Cl | H |
| I-226 | 3-naphthalen-2-yl-allyl | Cl | H | Cl | H |
| I-227 | 3-(5-trifluoromethyl-pyridin-2-yl)-allyl | Cl | H | Cl | H |
| I-228 | 3-(5-chloro-pyridin-2-yl)-allyl | Cl | H | Cl | H |
| I-229 | 3-pyridin-4-yl-allyl | Cl | H | Cl | H |
| I-230 | 3-(2-Chloro-pyridin-4-yl)-allyl | Cl | H | Cl | H |
| I-231 | 4-chlorobenzyl | Cl | H | H | Cl |
| I-232 | Cinnamyl | Cl | H | H | Cl |
| I-233 | 4-chlorocinnamyl | Cl | H | H | Cl |
| I-234 | 4-fluorocinnamyl | Cl | H | H | Cl |
| I-235 | 4-bromocinnamyl | Cl | H | H | Cl |
| I-236 | 4-trifluoromethylcinnamyl | Cl | H | H | Cl |
| I-237 | 4-trifluoromethoxycinnamyl | Cl | H | H | Cl |
| I-238 | 4-pentafluoroethoxycinnamyl | Cl | H | H | Cl |
| I-239 | 4-methoxycinnamyl | Cl | H | H | Cl |
| I-240 | 4-ethoxycinnamyl | Cl | H | H | Cl |
| I-241 | 4-cyanocinnamyl | Cl | H | H | Cl |
| I-242 | 3-(6-chloro-pyridin-3-yl)-allyl | Cl | H | H | Cl |
| I-243 | 3-(4-chlorophenyl)-but-2-enyl | Cl | H | H | Cl |
| I-244 | 3-(4-chlorophenyl)-3-fluoro-allyl | Cl | H | H | Cl |
| I-245 | 3-chloro-4-fluoro-cinnamyl | Cl | H | H | Cl |
| I-246 | 3,5-dichloro-cinnamyl | Cl | H | H | Cl |
| I-247 | 5-phenyl-penta-2,4-dienyl | Cl | H | H | Cl |
| I-248 | 4-isopropyloxycarbonylamino-cinnamyl | Cl | H | H | Cl |
| I-249 | 3-naphthalen-2-yl-allyl | Cl | H | H | Cl |
| I-250 | 3-(5-trifluoromethyl-pyridin-2-yl)-allyl | Cl | H | H | Cl |
| I-251 | 3-(5-chloro-pyridin-2-yl)-allyl | Cl | H | H | Cl |
| I-252 | 3-pyridin-4-yl-allyl | Cl | H | H | Cl |
| I-253 | 3-(2-Chloro-pyridin-4-yl)-allyl | Cl | H | H | Cl |
| I-254 | 4-chlorobenzyl | F | Cl | H | H |
| I-255 | Cinnamyl | F | Cl | H | H |
| I-256 | 4-chlorocinnamyl | F | Cl | H | H |
| I-257 | 4-fluorocinnamyl | F | Cl | H | H |
| I-258 | 4-bromocinnamyl | F | Cl | H | H |
| I-259 | 4-trifluoromethylcinnamyl | F | Cl | H | H |
| I-260 | 4-trifluoromethoxycinnamyl | F | Cl | H | H |
| I-261 | 4-pentafluoroethoxycinnamyl | F | Cl | H | H |
| I-262 | 4-methoxycinnamyl | F | Cl | H | H |
| I-263 | 4-ethoxycinnamyl | F | Cl | H | H |
| I-264 | 4-cyanocinnamyl | F | Cl | H | H |
| I-265 | 3-(6-chloro-pyridin-3-yl)-allyl | F | Cl | H | H |
| I-266 | 3-(4-chlorophenyl)-but-2-enyl | F | Cl | H | H |
| I-267 | 3-(4-chlorophenyl)-3-fluoro-allyl | F | Cl | H | H |
| I-268 | 3-chloro-4-fluoro-cinnamyl | F | Cl | H | H |
| I-269 | 3,5-dichloro-cinnamyl | F | Cl | H | H |
| I-270 | 5-phenyl-penta-2,4-dienyl | F | Cl | H | H |
| I-271 | 4-isopropyloxycarbonylamino-cinnamyl | F | Cl | H | H |
| I-272 | 3-naphthalen-2-yl-allyl | F | Cl | H | H |
| I-273 | 3-(5-trifluoromethyl-pyridin-2-yl)-allyl | F | Cl | H | H |
| I-274 | 3-(5-chloro-pyridin-2-yl)-allyl | F | Cl | H | H |
| I-275 | 3-pyridin-4-yl-allyl | F | Cl | H | H |
| I-276 | 3-(2-Chloro-pyridin-4-yl)-allyl | F | Cl | H | H |
| I-277 | 4-chlorobenzyl | F | H | Cl | H |
| I-278 | Cinnamyl | F | H | Cl | H |
| I-279 | 4-chlorocinnamyl | F | H | Cl | H |
| I-280 | 4-fluorocinnamyl | F | H | Cl | H |
| I-281 | 4-bromocinnamyl | F | H | Cl | H |
| I-282 | 4-trifluoromethylcinnamyl | F | H | Cl | H |
| I-283 | 4-trifluoromethoxycinnamyl | F | H | Cl | H |
| I-284 | 4-pentafluoroethoxycinnamyl | F | H | Cl | H |
| I-285 | 4-methoxycinnamyl | F | H | Cl | H |
| I-286 | 4-ethoxycinnamyl | F | H | Cl | H |
| I-287 | 4-cyanocinnamyl | F | H | Cl | H |
| I-288 | 3-(6-chloro-pyridin-3-yl)-allyl | F | H | Cl | H |
| I-289 | 3-(4-chlorophenyl)-but-2-enyl | F | H | Cl | H |
| I-290 | 3-(4-chlorophenyl)-3-fluoro-allyl | F | H | Cl | H |
| I-291 | 3-chloro-4-fluoro-cinnamyl | F | H | Cl | H |
| I-292 | 3,5-dichloro-cinnamyl | F | H | Cl | H |
| I-293 | 5-phenyl-penta-2,4-dienyl | F | H | Cl | H |
| I-294 | 4-isopropyloxycarbonylamino-cinnamyl | F | H | Cl | H |
| I-295 | 3-naphthalen-2-yl-allyl | F | H | Cl | H |
| I-296 | 3-(5-trifluoromethyl-pyridin-2-yl)-allyl | F | H | Cl | H |
| I-297 | 3-(5-chloro-pyridin-2-yl)-allyl | F | H | Cl | H |
| I-298 | 3-pyridin-4-yl-allyl | F | H | Cl | H |
| I-299 | 3-(2-Chloro-pyridin-4-yl)-allyl | F | H | Cl | H |
| I-300 | 4-chlorobenzyl | F | H | H | Cl |
| I-301 | Cinnamyl | F | H | H | Cl |
| I-302 | 4-chlorocinnamyl | F | H | H | Cl |
| I-303 | 4-fluorocinnamyl | F | H | H | Cl |
| I-304 | 4-bromocinnamyl | F | H | H | Cl |
| I-305 | 4-trifluoromethylcinnamyl | F | H | H | Cl |
| I-306 | 4-trifluoromethoxycinnamyl | F | H | H | Cl |
| I-307 | 4-pentafluoroethoxycinnamyl | F | H | H | Cl |
| I-308 | 4-methoxycinnamyl | F | H | H | Cl |
| I-309 | 4-ethoxycinnamyl | F | H | H | Cl |
| I-310 | 4-cyanocinnamyl | F | H | H | Cl |
| I-311 | 3-(6-chloro-pyridin-3-yl)-allyl | F | H | H | Cl |
| I-312 | 3-(4-chlorophenyl)-but-2-enyl | F | H | H | Cl |
| I-313 | 3-(4-chlorophenyl)-3-fluoro-allyl | F | H | H | Cl |
| I-314 | 3-chloro-4-fluoro-cinnamyl | F | H | H | Cl |
| I-315 | 3,5-dichloro-cinnamyl | F | H | H | Cl |
| I-316 | 5-phenyl-penta-2,4-dienyl | F | H | H | Cl |
| I-317 | 4-isopropyloxycarbonylamino-cinnamyl | F | H | H | Cl |
| I-318 | 3-naphthalen-2-yl-allyl | F | H | H | Cl |
| I-319 | 3-(5-trifluoromethyl-pyridin-2-yl)-allyl | F | H | H | Cl |
| I-320 | 3-(5-chloro-pyridin-2-yl)-allyl | F | H | H | Cl |
| I-321 | 3-pyridin-4-yl-allyl | F | H | H | Cl |
| I-322 | 3-(2-Chloro-pyridin-4-yl)-allyl | F | H | H | Cl |
| I-323 | 4-chlorobenzyl | Cl | F | H | H |
| I-324 | Cinnamyl | Cl | F | H | H |
| I-325 | 4-chlorocinnamyl | Cl | F | H | H |
| I-326 | 4-fluorocinnamyl | Cl | F | H | H |
| I-327 | 4-bromocinnamyl | Cl | F | H | H |
| I-328 | 4-trifluoromethylcinnamyl | Cl | F | H | H |
| I-329 | 4-trifluoromethoxycinnamyl | Cl | F | H | H |
| I-330 | 4-pentafluoroethoxycinnamyl | Cl | F | H | H |
| I-331 | 4-methoxycinnamyl | Cl | F | H | H |
| I-332 | 4-ethoxycinnamyl | Cl | F | H | H |
| I-333 | 4-cyanocinnamyl | Cl | F | H | H |
| I-334 | 3-(6-chloro-pyridin-3-yl)-allyl | Cl | F | H | H |
| I-335 | 3-(4-chlorophenyl)-but-2-enyl | Cl | F | H | H |
| I-336 | 3-(4-chlorophenyl)-3-fluoro-allyl | Cl | F | H | H |
| I-337 | 3-chloro-4-fluoro-cinnamyl | Cl | F | H | H |
| I-338 | 3,5-dichloro-cinnamyl | Cl | F | H | H |
| I-339 | 5-phenyl-penta-2,4-dienyl | Cl | F | H | H |
| I-340 | 4-isopropyloxycarbonylamino-cinnamyl | Cl | F | H | H |
| I-341 | 3-naphthalen-2-yl-allyl | Cl | F | H | H |
| I-342 | 3-(5-trifluoromethyl-pyridin-2-yl)-allyl | Cl | F | H | H |
| I-343 | 3-(5-chloro-pyridin-2-yl)-allyl | Cl | F | H | H |
| I-344 | 3-pyridin-4-yl-allyl | Cl | F | H | H |
| I-345 | 3-(2-Chloro-pyridin-4-yl)-allyl | Cl | F | H | H |
| I-346 | 4-chlorobenzyl | H | F | Cl | H |
| I-347 | Cinnamyl | H | F | Cl | H |
| I-348 | 4-chlorocinnamyl | H | F | Cl | H |
| I-349 | 4-fluorocinnamyl | H | F | Cl | H |
| I-350 | 4-bromocinnamyl | H | F | Cl | H |
| I-351 | 4-trifluoromethylcinnamyl | H | F | Cl | H |
| I-352 | 4-trifluoromethoxycinnamyl | H | F | Cl | H |
| I-353 | 4-pentafluoroethoxycinnamyl | H | F | Cl | H |
| I-354 | 4-methoxycinnamyl | H | F | Cl | H |
| I-355 | 4-ethoxycinnamyl | H | F | Cl | H |
| I-356 | 4-cyanocinnamyl | H | F | Cl | H |
| I-357 | 3-(6-chloro-pyridin-3-yl)-allyl | H | F | Cl | H |

TABLE 1-continued

| Compound No | R⁸ | Rᵃ | Rᵇ | Rᶜ | Rᵈ |
|---|---|---|---|---|---|
| I-358 | 3-(4-chlorophenyl)-but-2-enyl | H | F | Cl | H |
| I-359 | 3-(4-chlorophenyl)-3-fluoro-allyl | H | F | Cl | H |
| I-360 | 3-chloro-4-fluoro-cinnamyl | H | F | Cl | H |
| I-361 | 3,5-dichloro-cinnamyl | H | F | Cl | H |
| I-362 | 5-phenyl-penta-2,4-dienyl | H | F | Cl | H |
| I-363 | 4-isopropyloxycarbonylamino-cinnamyl | H | F | Cl | H |
| I-364 | 3-naphthalen-2-yl-allyl | H | F | Cl | H |
| I-365 | 3-(5-trifluoromethyl-pyridin-2-yl)-allyl | H | F | Cl | H |
| I-366 | 3-(5-chloro-pyridin-2-yl)-allyl | H | F | Cl | H |
| I-367 | 3-pyridin-4-yl-allyl | H | F | Cl | H |
| I-368 | 3-(2-Chloro-pyridin-4-yl)-allyl | H | F | Cl | H |
| I-369 | 4-chlorobenzyl | H | F | H | Cl |
| I-370 | Cinnamyl | H | F | H | Cl |
| I-371 | 4-chlorocinnamyl | H | F | H | Cl |
| I-372 | 4-fluorocinnamyl | H | F | H | Cl |
| I-373 | 4-bromocinnamyl | H | F | H | Cl |
| I-374 | 4-trifluoromethylcinnamyl | H | F | H | Cl |
| I-375 | 4-trifluoromethoxycinnamyl | H | F | H | Cl |
| I-376 | 4-pentafluoroethoxycinnamyl | H | F | H | Cl |
| I-377 | 4-methoxycinnamyl | H | F | H | Cl |
| I-378 | 4-ethoxycinnamyl | H | F | H | Cl |
| I-379 | 4-cyanocinnamyl | H | F | H | Cl |
| I-380 | 3-(6-chloro-pyridin-3-yl)-allyl | H | F | H | Cl |
| I-381 | 3-(4-chlorophenyl)-but-2-enyl | H | F | H | Cl |
| I-382 | 3-(4-chlorophenyl)-3-fluoro-allyl | H | F | H | Cl |
| I-383 | 3-chloro-4-fluoro-cinnamyl | H | F | H | Cl |
| I-384 | 3,5-dichloro-cinnamyl | H | F | H | Cl |
| I-385 | 5-phenyl-penta-2,4-dienyl | H | F | H | Cl |
| I-386 | 4-isopropyloxycarbonylamino-cinnamyl | H | F | H | Cl |
| I-387 | 3-naphthalen-2-yl-allyl | H | F | H | Cl |
| I-388 | 3-(5-trifluoromethyl-pyridin-2-yl)-allyl | H | F | H | Cl |
| I-389 | 3-(5-chloro-pyridin-2-yl)-allyl | H | F | H | Cl |
| I-390 | 3-pyridin-4-yl-allyl | H | F | H | Cl |
| I-391 | 3-(2-Chloro-pyridin-4-yl)-allyl | H | F | H | Cl |
| I-392 | 4-chlorobenzyl | Cl | H | F | H |
| I-393 | Cinnamyl | Cl | H | F | H |
| I-394 | 4-chlorocinnamyl | Cl | H | F | H |
| I-395 | 4-fluorocinnamyl | Cl | H | F | H |
| I-396 | 4-bromocinnamyl | Cl | H | F | H |
| I-397 | 4-trifluoromethylcinnamyl | Cl | H | F | H |
| I-398 | 4-trifluoromethoxycinnamyl | Cl | H | F | H |
| I-399 | 4-pentafluoroethoxycinnamyl | Cl | H | F | H |
| I-400 | 4-methoxycinnamyl | Cl | H | F | H |
| I-401 | 4-ethoxycinnamyl | Cl | H | F | H |
| I-402 | 4-cyanocinnamyl | Cl | H | F | H |
| I-403 | 3-(6-chloro-pyridin-3-yl)-allyl | Cl | H | F | H |
| I-404 | 3-(4-chlorophenyl)-but-2-enyl | Cl | H | F | H |
| I-405 | 3-(4-chlorophenyl)-3-fluoro-allyl | Cl | H | F | H |
| I-406 | 3-chloro-4-fluoro-cinnamyl | Cl | H | F | H |
| I-407 | 3,5-dichloro-cinnamyl | Cl | H | F | H |
| I-408 | 5-phenyl-penta-2,4-dienyl | Cl | H | F | H |
| I-409 | 4-isopropyloxycarbonylamino-cinnamyl | Cl | H | F | H |
| I-410 | 3-naphthalen-2-yl-allyl | Cl | H | F | H |
| I-411 | 3-(5-trifluoromethyl-pyridin-2-yl)-allyl | Cl | H | F | H |
| I-412 | 3-(5-chloro-pyridin-2-yl)-allyl | Cl | H | F | H |
| I-413 | 3-pyridin-4-yl-allyl | Cl | H | F | H |
| I-414 | 3-(2-Chloro-pyridin-4-yl)-allyl | Cl | H | F | H |
| I-415 | 4-chlorobenzyl | H | Cl | F | H |
| I-416 | Cinnamyl | H | Cl | F | H |
| I-417 | 4-chlorocinnamyl | H | Cl | F | H |
| I-418 | 4-fluorocinnamyl | H | Cl | F | H |
| I-419 | 4-bromocinnamyl | H | Cl | F | H |
| I-420 | 4-trifluoromethylcinnamyl | H | Cl | F | H |
| I-421 | 4-trifluoromethoxycinnamyl | H | Cl | F | H |
| I-422 | 4-pentafluoroethoxycinnamyl | H | Cl | F | H |
| I-423 | 4-methoxycinnamyl | H | Cl | F | H |
| I-424 | 4-ethoxycinnamyl | H | Cl | F | H |
| I-425 | 4-cyanocinnamyl | H | Cl | F | H |
| I-426 | 3-(6-chloro-pyridin-3-yl)-allyl | H | Cl | F | H |
| I-427 | 3-(4-chlorophenyl)-but-2-enyl | H | Cl | F | H |
| I-428 | 3-(4-chlorophenyl)-3-fluoro-allyl | H | Cl | F | H |
| I-429 | 3-chloro-4-fluoro-cinnamyl | H | Cl | F | H |
| I-430 | 3,5-dichloro-cinnamyl | H | Cl | F | H |
| I-431 | 5-phenyl-penta-2,4-dienyl | H | Cl | F | H |
| I-432 | 4-isopropyloxycarbonylamino-cinnamyl | H | Cl | F | H |
| I-433 | 3-naphthalen-2-yl-allyl | H | Cl | F | H |
| I-434 | 3-(5-trifluoromethyl-pyridin-2-yl)-allyl | H | Cl | F | H |
| I-435 | 3-(5-chloro-pyridin-2-yl)-allyl | H | Cl | F | H |
| I-436 | 3-pyridin-4-yl-allyl | H | Cl | F | H |
| I-437 | 3-(2-Chloro-pyridin-4-yl)-allyl | H | Cl | F | H |
| I-438 | 4-chlorobenzyl | H | H | F | Cl |
| I-439 | Cinnamyl | H | H | F | Cl |
| I-440 | 4-chlorocinnamyl | H | H | F | Cl |
| I-441 | 4-fluorocinnamyl | H | H | F | Cl |
| I-442 | 4-bromocinnamyl | H | H | F | Cl |
| I-443 | 4-trifluoromethylcinnamyl | H | H | F | Cl |
| I-444 | 4-trifluoromethoxycinnamyl | H | H | F | Cl |
| I-445 | 4-pentafluoroethoxycinnamyl | H | H | F | Cl |
| I-446 | 4-methoxycinnamyl | H | H | F | Cl |
| I-447 | 4-ethoxycinnamyl | H | H | F | Cl |
| I-448 | 4-cyanocinnamyl | H | H | F | Cl |
| I-449 | 3-(6-chloro-pyridin-3-yl)-allyl | H | H | F | Cl |
| I-450 | 3-(4-chlorophenyl)-but-2-enyl | H | H | F | Cl |
| I-451 | 3-(4-chlorophenyl)-3-fluoro-allyl | H | H | F | Cl |
| I-452 | 3-chloro-4-fluoro-cinnamyl | H | H | F | Cl |
| I-453 | 3,5-dichloro-cinnamyl | H | H | F | Cl |
| I-454 | 5-phenyl-penta-2,4-dienyl | H | H | F | Cl |
| I-455 | 4-isopropyloxycarbonylamino-cinnamyl | H | H | F | Cl |
| I-456 | 3-naphthalen-2-yl-allyl | H | H | F | Cl |
| I-457 | 3-(5-trifluoromethyl-pyridin-2-yl)-allyl | H | H | F | Cl |
| I-458 | 3-(5-chloro-pyridin-2-yl)-allyl | H | H | F | Cl |
| I-459 | 3-pyridin-4-yl-allyl | H | H | F | Cl |
| I-460 | 3-(2-Chloro-pyridin-4-yl)-allyl | H | H | F | Cl |
| I-461 | 4-chlorobenzyl | Cl | H | H | F |
| I-462 | Cinnamyl | Cl | H | H | F |
| I-463 | 4-chlorocinnamyl | Cl | H | H | F |
| I-464 | 4-fluorocinnamyl | Cl | H | H | F |
| I-465 | 4-bromocinnamyl | Cl | H | H | F |
| I-466 | 4-trifluoromethylcinnamyl | Cl | H | H | F |
| I-467 | 4-trifluoromethoxycinnamyl | Cl | H | H | F |
| I-468 | 4-pentafluoroethoxycinnamyl | Cl | H | H | F |
| I-469 | 4-methoxycinnamyl | Cl | H | H | F |
| I-470 | 4-ethoxycinnamyl | Cl | H | H | F |
| I-471 | 4-cyanocinnamyl | Cl | H | H | F |
| I-472 | 3-(6-chloro-pyridin-3-yl)-allyl | Cl | H | H | F |
| I-473 | 3-(4-chlorophenyl)-but-2-enyl | Cl | H | H | F |
| I-474 | 3-(4-chlorophenyl)-3-fluoro-allyl | Cl | H | H | F |
| I-475 | 3-chloro-4-fluoro-cinnamyl | Cl | H | H | F |
| I-476 | 3,5-dichloro-cinnamyl | Cl | H | H | F |
| I-477 | 5-phenyl-penta-2,4-dienyl | Cl | H | H | F |
| I-478 | 4-isopropyloxycarbonylamino-cinnamyl | Cl | H | H | F |
| I-479 | 3-naphthalen-2-yl-allyl | Cl | H | H | F |
| I-480 | 3-(5-trifluoromethyl-pyridin-2-yl)-allyl | Cl | H | H | F |
| I-481 | 3-(5-chloro-pyridin-2-yl)-allyl | Cl | H | H | F |
| I-482 | 3-pyridin-4-yl-allyl | Cl | H | H | F |
| I-483 | 3-(2-Chloro-pyridin-4-yl)-allyl | Cl | H | H | F |
| I-484 | 4-chlorobenzyl | H | Cl | H | F |
| I-485 | Cinnamyl | H | Cl | H | F |
| I-486 | 4-chlorocinnamyl | H | Cl | H | F |
| I-487 | 4-fluorocinnamyl | H | Cl | H | F |
| I-488 | 4-bromocinnamyl | H | Cl | H | F |
| I-489 | 4-trifluoromethylcinnamyl | H | Cl | H | F |
| I-490 | 4-trifluoromethoxycinnamyl | H | Cl | H | F |
| I-491 | 4-pentafluoroethoxycinnamyl | H | Cl | H | F |
| I-492 | 4-methoxycinnamyl | H | Cl | H | F |
| I-493 | 4-ethoxycinnamyl | H | Cl | H | F |

TABLE 1-continued

| Compound No | R⁸ | Rᵃ | Rᵇ | Rᶜ | Rᵈ |
|---|---|---|---|---|---|
| I-494 | 4-cyanocinnamyl | H | Cl | H | F |
| I-495 | 3-(6-chloro-pyridin-3-yl)-allyl | H | Cl | H | F |
| I-496 | 3-(4-chlorophenyl)-but-2-enyl | H | Cl | H | F |
| I-497 | 3-(4-chlorophenyl)-3-fluoro-allyl | H | Cl | H | F |
| I-498 | 3-chloro-4-fluoro-cinnamyl | H | Cl | H | F |
| I-499 | 3,5-dichloro-cinnamyl | H | Cl | H | F |
| I-500 | 5-phenyl-penta-2,4-dienyl | H | Cl | H | F |
| I-501 | 4-isopropyloxycarbonylamino-cinnamyl | H | Cl | H | F |
| I-502 | 3-naphthalen-2-yl-allyl | H | Cl | H | F |
| I-503 | 3-(5-trifluoromethyl-pyridin-2-yl)-allyl | H | Cl | H | F |
| I-504 | 3-(5-chloro-pyridin-2-yl)-allyl | H | Cl | H | F |
| I-505 | 3-pyridin-4-yl-allyl | H | Cl | H | F |
| I-506 | 3-(2-Chloro-pyridin-4-yl)-allyl | H | Cl | H | F |
| I-507 | 4-chlorobenzyl | H | H | Cl | F |
| I-508 | Cinnamyl | H | H | Cl | F |
| I-509 | 4-chlorocinnamyl | H | H | Cl | F |
| I-510 | 4-fluorocinnamyl | H | H | Cl | F |
| I-511 | 4-bromocinnamyl | H | H | Cl | F |
| I-512 | 4-trifluoromethylcinnamyl | H | H | Cl | F |
| I-513 | 4-trifluoromethoxycinnamyl | H | H | Cl | F |
| I-514 | 4-pentafluoroethoxycinnamyl | H | H | Cl | F |
| I-515 | 4-methoxycinnamyl | H | H | Cl | F |
| I-516 | 4-ethoxycinnamyl | H | H | Cl | F |
| I-517 | 4-cyanocinnamyl | H | H | Cl | F |
| I-518 | 3-(6-chloro-pyridin-3-yl)-allyl | H | H | Cl | F |
| I-519 | 3-(4-chlorophenyl)-but-2-enyl | H | H | Cl | F |
| I-520 | 3-(4-chlorophenyl)-3-fluoro-allyl | H | H | Cl | F |
| I-521 | 3-chloro-4-fluoro-cinnamyl | H | H | Cl | F |
| I-522 | 3,5-dichloro-cinnamyl | H | H | Cl | F |
| I-523 | 5-phenyl-penta-2,4-dienyl | H | H | Cl | F |
| I-524 | 4-isopropyloxycarbonylamino-cinnamyl | H | H | Cl | F |
| I-525 | 3-naphthalen-2-yl-allyl | H | H | Cl | F |
| I-526 | 3-(5-trifluoromethyl-pyridin-2-yl)-allyl | H | H | Cl | F |
| I-527 | 3-(5-chloro-pyridin-2-yl)-allyl | H | H | Cl | F |
| I-528 | 3-pyridin-4-yl-allyl | H | H | Cl | F |
| I-529 | 3-(2-Chloro-pyridin-4-yl)-allyl | H | H | Cl | F |
| I-530 | 4-chlorobenzyl | H | F | F | F |
| I-531 | Cinnamyl | H | F | F | F |
| I-532 | 4-chlorocinnamyl | H | F | F | F |
| I-533 | 4-fluorocinnamyl | H | F | F | F |
| I-534 | 4-bromocinnamyl | H | F | F | F |
| I-535 | 4-trifluoromethylcinnamyl | H | F | F | F |
| I-536 | 4-trifluoromethoxycinnamyl | H | F | F | F |
| I-537 | 4-pentafluoroethoxycinnamyl | H | F | F | F |
| I-538 | 4-methoxycinnamyl | H | F | F | F |
| I-539 | 4-ethoxycinnamyl | H | F | F | F |
| I-540 | 4-cyanocinnamyl | H | F | F | F |
| I-541 | 3-(6-chloro-pyridin-3-yl)-allyl | H | F | F | F |
| I-542 | 3-(4-chlorophenyl)-but-2-enyl | H | F | F | F |
| I-543 | 3-(4-chlorophenyl)-3-fluoro-allyl | H | F | F | F |
| I-544 | 3-chloro-4-fluoro-cinnamyl | H | F | F | F |
| I-545 | 3,5-dichloro-cinnamyl | H | F | F | F |
| I-546 | 5-phenyl-penta-2,4-dienyl | H | F | F | F |
| I-547 | 4-isopropyloxycarbonylamino-cinnamyl | H | F | F | F |
| I-548 | 3-naphthalen-2-yl-allyl | H | F | F | F |
| I-549 | 3-(5-trifluoromethyl-pyridin-2-yl)-allyl | H | F | F | F |
| I-550 | 3-(5-chloro-pyridin-2-yl)-allyl | H | F | F | F |
| I-551 | 3-pyridin-4-yl-allyl | H | F | F | F |
| I-552 | 3-(2-Chloro-pyridin-4-yl)-allyl | H | F | F | F |
| I-553 | 4-chlorobenzyl | F | H | F | F |
| I-554 | Cinnamyl | F | H | F | F |
| I-555 | 4-chlorocinnamyl | F | H | F | F |
| I-556 | 4-fluorocinnamyl | F | H | F | F |
| I-557 | 4-bromocinnamyl | F | H | F | F |
| I-558 | 4-trifluoromethylcinnamyl | F | H | F | F |
| I-559 | 4-trifluoromethoxycinnamyl | F | H | F | F |
| I-560 | 4-pentafluoroethoxycinnamyl | F | H | F | F |
| I-561 | 4-methoxycinnamyl | F | H | F | F |
| I-562 | 4-ethoxycinnamyl | F | H | F | F |
| I-563 | 4-cyanocinnamyl | F | H | F | F |
| I-564 | 3-(6-chloro-pyridin-3-yl)-allyl | F | H | F | F |
| I-565 | 3-(4-chlorophenyl)-but-2-enyl | F | H | F | F |
| I-566 | 3-(4-chlorophenyl)-3-fluoro-allyl | F | H | F | F |
| I-567 | 3-chloro-4-fluoro-cinnamyl | F | H | F | F |
| I-568 | 3,5-dichloro-cinnamyl | F | H | F | F |
| I-569 | 5-phenyl-penta-2,4-dienyl | F | H | F | F |
| I-570 | 4-isopropyloxycarbonylamino-cinnamyl | F | H | F | F |
| I-571 | 3-naphthalen-2-yl-allyl | F | H | F | F |
| I-572 | 3-(5-trifluoromethyl-pyridin-2-yl)-allyl | F | H | F | F |
| I-573 | 3-(5-chloro-pyridin-2-yl)-allyl | F | H | F | F |
| I-574 | 3-pyridin-4-yl-allyl | F | H | F | F |
| I-575 | 3-(2-Chloro-pyridin-4-yl)-allyl | F | H | F | F |
| I-576 | 4-chlorobenzyl | F | F | H | F |
| I-577 | Cinnamyl | F | F | H | F |
| I-578 | 4-chlorocinnamyl | F | F | H | F |
| I-579 | 4-fluorocinnamyl | F | F | H | F |
| I-580 | 4-bromocinnamyl | F | F | H | F |
| I-581 | 4-trifluoromethylcinnamyl | F | F | H | F |
| I-582 | 4-trifluoromethoxycinnamyl | F | F | H | F |
| I-583 | 4-pentafluoroethoxycinnamyl | F | F | H | F |
| I-584 | 4-methoxycinnamyl | F | F | H | F |
| I-585 | 4-ethoxycinnamyl | F | F | H | F |
| I-586 | 4-cyanocinnamyl | F | F | H | F |
| I-587 | 3-(6-chloro-pyridin-3-yl)-allyl | F | F | H | F |
| I-588 | 3-(4-chlorophenyl)-but-2-enyl | F | F | H | F |
| I-589 | 3-(4-chlorophenyl)-3-fluoro-allyl | F | F | H | F |
| I-590 | 3-chloro-4-fluoro-cinnamyl | F | F | H | F |
| I-591 | 3,5-dichloro-cinnamyl | F | F | H | F |
| I-592 | 5-phenyl-penta-2,4-dienyl | F | F | H | F |
| I-593 | 4-isopropyloxycarbonylamino-cinnamyl | F | F | H | F |
| I-594 | 3-naphthalen-2-yl-allyl | F | F | H | F |
| I-595 | 3-(5-trifluoromethyl-pyridin-2-yl)-allyl | F | F | H | F |
| I-596 | 3-(5-chloro-pyridin-2-yl)-allyl | F | F | H | F |
| I-597 | 3-pyridin-4-yl-allyl | F | F | H | F |
| I-598 | 3-(2-Chloro-pyridin-4-yl)-allyl | F | F | H | F |
| I-599 | 4-chlorobenzyl | F | F | F | H |
| I-600 | Cinnamyl | F | F | F | H |
| I-601 | 4-chlorocinnamyl | F | F | F | H |
| I-602 | 4-fluorocinnamyl | F | F | F | H |
| I-603 | 4-bromocinnamyl | F | F | F | H |
| I-604 | 4-trifluoromethylcinnamyl | F | F | F | H |
| I-605 | 4-trifluoromethoxycinnamyl | F | F | F | H |
| I-606 | 4-pentafluoroethoxycinnamyl | F | F | F | H |
| I-607 | 4-methoxycinnamyl | F | F | F | H |
| I-608 | 4-ethoxycinnamyl | F | F | F | H |
| I-609 | 4-cyanocinnamyl | F | F | F | H |
| I-610 | 3-(6-chloro-pyridin-3-yl)-allyl | F | F | F | H |
| I-611 | 3-(4-chlorophenyl)-but-2-enyl | F | F | F | H |
| I-612 | 3-(4-chlorophenyl)-3-fluoro-allyl | F | F | F | H |
| I-613 | 3-chloro-4-fluoro-cinnamyl | F | F | F | H |
| I-614 | 3,5-dichloro-cinnamyl | F | F | F | H |
| I-615 | 5-phenyl-penta-2,4-dienyl | F | F | F | H |
| I-616 | 4-isopropyloxycarbonylamino-cinnamyl | F | F | F | H |
| I-617 | 3-naphthalen-2-yl-allyl | F | F | F | H |
| I-618 | 3-(5-trifluoromethyl-pyridin-2-yl)-allyl | F | F | F | H |
| I-619 | 3-(5-chloro-pyridin-2-yl)-allyl | F | F | F | H |
| I-620 | 3-pyridin-4-yl-allyl | F | F | F | H |
| I-621 | 3-(2-Chloro-pyridin-4-yl)-allyl | F | F | F | H |
| I-622 | 4-chlorobenzyl | H | Cl | Cl | Cl |
| I-623 | Cinnamyl | H | Cl | Cl | Cl |
| I-624 | 4-chlorocinnamyl | H | Cl | Cl | Cl |
| I-625 | 4-fluorocinnamyl | H | Cl | Cl | Cl |
| I-626 | 4-bromocinnamyl | H | Cl | Cl | Cl |
| I-627 | 4-trifluoromethylcinnamyl | H | Cl | Cl | Cl |
| I-628 | 4-trifluoromethoxycinnamyl | H | Cl | Cl | Cl |
| I-629 | 4-pentafluoroethoxycinnamyl | H | Cl | Cl | Cl |

TABLE 1-continued

| Compound No | R8 | Rª | Rᵇ | Rᶜ | Rᵈ |
|---|---|---|---|---|---|
| I-630 | 4-methoxycinnamyl | H | Cl | Cl | Cl |
| I-631 | 4-ethoxycinnamyl | H | Cl | Cl | Cl |
| I-632 | 4-cyanocinnamyl | H | Cl | Cl | Cl |
| I-633 | 3-(6-chloro-pyridin-3-yl)-allyl | H | Cl | Cl | Cl |
| I-634 | 3-(4-chlorophenyl)-but-2-enyl | H | Cl | Cl | Cl |
| I-635 | 3-(4-chlorophenyl)-3-fluoro-allyl | H | Cl | Cl | Cl |
| I-636 | 3-chloro-4-fluoro-cinnamyl | H | Cl | Cl | Cl |
| I-637 | 3,5-dichloro-cinnamyl | H | Cl | Cl | Cl |
| I-638 | 5-phenyl-penta-2,4-dienyl | H | Cl | Cl | Cl |
| I-639 | 4-isopropyloxycarbonylamino-cinnamyl | H | Cl | Cl | Cl |
| I-640 | 3-naphthalen-2-yl-allyl | H | Cl | Cl | Cl |
| I-641 | 3-(5-trifluoromethyl-pyridin-2-yl)-allyl | H | Cl | Cl | Cl |
| I-642 | 3-(5-chloro-pyridin-2-yl)-allyl | H | Cl | Cl | Cl |
| I-643 | 3-pyridin-4-yl-allyl | H | Cl | Cl | Cl |
| I-644 | 3-(2-Chloro-pyridin-4-yl)-allyl | H | Cl | Cl | Cl |
| I-645 | 4-chlorobenzyl | Cl | H | Cl | Cl |
| I-646 | Cinnamyl | Cl | H | Cl | Cl |
| I-647 | 4-chlorocinnamyl | Cl | H | Cl | Cl |
| I-648 | 4-fluorocinnamyl | Cl | H | Cl | Cl |
| I-649 | 4-bromocinnamyl | Cl | H | Cl | Cl |
| I-650 | 4-trifluoromethylcinnamyl- | Cl | H | Cl | Cl |
| I-651 | 4-trifluoromethoxycinnamyl | Cl | H | Cl | Cl |
| I-652 | 4-pentafluoroethoxycinnamyl | Cl | H | Cl | Cl |
| I-653 | 4-methoxycinnamyl | Cl | H | Cl | Cl |
| I-654 | 4-ethoxycinnamyl | Cl | H | Cl | Cl |
| I-655 | 4-cyanocinnamyl | Cl | H | Cl | Cl |
| I-656 | 3-(6-chloro-pyridin-3-yl)-allyl | Cl | H | Cl | Cl |
| I-657 | 3-(4-chlorophenyl)-but-2-enyl | Cl | H | Cl | Cl |
| I-658 | 3-(4-chlorophenyl)-3-fluoro-allyl | Cl | H | Cl | Cl |
| I-659 | 3-chloro-4-fluoro-cinnamyl | Cl | H | Cl | Cl |
| I-660 | 3,5-dichloro-cinnamyl | Cl | H | Cl | Cl |
| I-661 | 5-phenyl-penta-2,4-dienyl | Cl | H | Cl | Cl |
| I-662 | 4-isopropyloxycarbonylamino-cinnamyl | Cl | H | Cl | Cl |
| I-663 | 3-naphthalen-2-yl-allyl | Cl | H | Cl | Cl |
| I-664 | 3-(5-trifluoromethyl-pyridin-2-yl)-allyl | Cl | H | Cl | Cl |
| I-665 | 3-(5-chloro-pyridin-2-yl)-allyl | Cl | H | Cl | Cl |
| I-666 | 3-pyridin-4-yl-allyl | Cl | H | Cl | Cl |
| I-667 | 3-(2-Chloro-pyridin-4-yl)-allyl | Cl | H | Cl | Cl |
| I-668 | 4-chlorobenzyl | Cl | Cl | H | Cl |
| I-669 | Cinnamyl | Cl | Cl | H | Cl |
| I-670 | 4-chlorocinnamyl | Cl | Cl | H | Cl |
| I-671 | 4-fluorocinnamyl | Cl | Cl | H | Cl |
| I-672 | 4-bromocinnamyl | Cl | Cl | H | Cl |
| I-673 | 4-trifluoromethylcinnamyl | Cl | Cl | H | Cl |
| I-674 | 4-trifluoromethoxycinnamyl | Cl | Cl | H | Cl |
| I-675 | 4-pentafluoroethoxycinnamyl | Cl | Cl | H | Cl |
| I-676 | 4-methoxycinnamyl | Cl | Cl | H | Cl |
| I-677 | 4-ethoxycinnamyl | Cl | Cl | H | Cl |
| I-678 | 4-cyanocinnamyl | Cl | Cl | H | Cl |
| I-679 | 3-(6-chloro-pyridin-3-yl)-allyl | Cl | Cl | H | Cl |
| I-680 | 3-(4-chlorophenyl)-but-2-enyl | Cl | Cl | H | Cl |
| I-681 | 3-(4-chlorophenyl)-3-fluoro-allyl | Cl | Cl | H | Cl |
| I-682 | 3-chloro-4-fluoro-cinnamyl | Cl | Cl | H | Cl |
| I-683 | 3,5-dichloro-cinnamyl | Cl | Cl | H | Cl |
| I-684 | 5-phenyl-penta-2,4-dienyl | Cl | Cl | H | Cl |
| I-685 | 4-isopropyloxycarbonylamino-cinnamyl | Cl | Cl | H | Cl |
| I-686 | 3-naphthalen-2-yl-allyl | Cl | Cl | H | Cl |
| I-687 | 3-(5-trifluoromethyl-pyridin-2-yl)-allyl | Cl | Cl | H | Cl |
| I-688 | 3-(5-chloro-pyridin-2-yl)-allyl | Cl | Cl | H | Cl |
| I-689 | 3-pyridin-4-yl-allyl | Cl | Cl | H | Cl |
| I-690 | 3-(2-Chloro-pyridin-4-yl)-allyl | Cl | Cl | H | Cl |
| I-691 | 4-chlorobenzyl | Cl | Cl | Cl | H |
| I-692 | Cinnamyl | Cl | Cl | Cl | H |
| I-693 | 4-chlorocinnamyl | Cl | Cl | Cl | H |
| I-694 | 4-fluorocinnamyl | Cl | Cl | Cl | H |
| I-695 | 4-bromocinnamyl | Cl | Cl | Cl | H |
| I-696 | 4-trifluoromethylcinnamyl | Cl | Cl | Cl | H |
| I-697 | 4-trifluoromethoxycinnamyl | Cl | Cl | Cl | H |
| I-698 | 4-pentafluoroethoxycinnamyl | Cl | Cl | Cl | H |
| I-699 | 4-methoxycinnamyl | Cl | Cl | Cl | H |
| I-700 | 4-ethoxycinnamyl | Cl | Cl | Cl | H |
| I-701 | 4-cyanocinnamyl | Cl | Cl | Cl | H |
| I-702 | 3-(6-chloro-pyridin-3-yl)-allyl | Cl | Cl | Cl | H |
| I-703 | 3-(4-chlorophenyl)-but-2-enyl | Cl | Cl | Cl | H |
| I-704 | 3-(4-chlorophenyl)-3-fluoro-allyl | Cl | Cl | Cl | H |
| I-705 | 3-chloro-4-fluoro-cinnamyl | Cl | Cl | Cl | H |
| I-706 | 3,5-dichloro-cinnamyl | Cl | Cl | Cl | H |
| I-707 | 5-phenyl-penta-2,4-dienyl | Cl | Cl | Cl | H |
| I-708 | 4-isopropyloxycarbonylamino-cinnamyl | Cl | Cl | Cl | H |
| I-709 | 3-naphthalen-2-yl-allyl | Cl | Cl | Cl | H |
| I-710 | 3-(5-trifluoromethyl-pyridin-2-yl)-allyl | Cl | Cl | Cl | H |
| I-711 | 3-(5-chloro-pyridin-2-yl)-allyl | Cl | Cl | Cl | H |
| I-712 | 3-pyridin-4-yl-allyl | Cl | Cl | Cl | H |
| I-713 | 3-(2-Chloro-pyridin-4-yl)-allyl | Cl | Cl | Cl | H |
| I-714 | 4-chlorobenzyl | Cl | Cl | Cl | Cl |
| I-715 | Cinnamyl | Cl | Cl | Cl | Cl |
| I-716 | 4-chlorocinnamyl | Cl | Cl | Cl | Cl |
| I-717 | 4-fluorocinnamyl | Cl | Cl | Cl | Cl |
| I-718 | 4-bromocinnamyl | Cl | Cl | Cl | Cl |
| I-719 | 4-trifluoromethylcinnamyl | Cl | Cl | Cl | Cl |
| I-720 | 4-trifluoromethoxycinnamyl | Cl | Cl | Cl | Cl |
| I-721 | 4-pentafluoroethoxycinnamyl | Cl | Cl | Cl | Cl |
| I-722 | 4-methoxycinnamyl | Cl | Cl | Cl | Cl |
| I-723 | 4-ethoxycinnamyl | Cl | Cl | Cl | Cl |
| I-724 | 4-cyanocinnamyl | Cl | Cl | Cl | Cl |
| I-725 | 3-(6-chloro-pyridin-3-yl)-allyl | Cl | Cl | Cl | Cl |
| I-726 | 3-(4-chlorophenyl)-but-2-enyl | Cl | Cl | Cl | Cl |
| I-727 | 3-(4-chlorophenyl)-3-fluoro-allyl | Cl | Cl | Cl | Cl |
| I-728 | 3-chloro-4-fluoro-cinnamyl | Cl | Cl | Cl | Cl |
| I-729 | 3,5-dichloro-cinnamyl | Cl | Cl | Cl | Cl |
| I-730 | 5-phenyl-penta-2,4-dienyl | Cl | Cl | Cl | Cl |
| I-731 | 4-isopropyloxycarbonylamino-cinnamyl | Cl | Cl | Cl | Cl |
| I-732 | 3-naphthalen-2-yl-allyl | Cl | Cl | Cl | Cl |
| I-733 | 3-(5-trifluoromethyl-pyridin-2-yl)-allyl | Cl | Cl | Cl | Cl |
| I-734 | 3-(5-chloro-pyridin-2-yl)-allyl | Cl | Cl | Cl | Cl |
| I-735 | 3-pyridin-4-yl-allyl | Cl | Cl | Cl | Cl |
| I-736 | 3-(2-Chloro-pyridin-4-yl)-allyl | Cl | Cl | Cl | Cl |
| I-737 | 4-chlorobenzyl | F | F | F | F |
| I-738 | Cinnamyl | F | F | F | F |
| I-739 | 4-chlorocinnamyl | F | F | F | F |
| I-740 | 4-fluorocinnamyl | F | F | F | F |
| I-741 | 4-bromocinnamyl | F | F | F | F |
| I-742 | 4-trifluoromethylcinnamyl | F | F | F | F |
| I-743 | 4-trifluoromethoxycinnamyl | F | F | F | F |
| I-744 | 4-pentafluoroethoxycinnamyl | F | F | F | F |
| I-745 | 4-methoxycinnamyl | F | F | F | F |
| I-746 | 4-ethoxycinnamyl | F | F | F | F |
| I-747 | 4-cyanocinnamyl | F | F | F | F |
| I-748 | 3-(6-chloro-pyridin-3-yl)-allyl | F | F | F | F |
| I-749 | 3-(4-chlorophenyl)-but-2-enyl | F | F | F | F |
| I-750 | 3-(4-chlorophenyl)-3-fluoro-allyl | F | F | F | F |
| I-751 | 3-chloro-4-fluoro-cinnamyl | F | F | F | F |
| I-752 | 3,5-dichloro-cinnamyl | F | F | F | F |
| I-753 | 5-phenyl-penta-2,4-dienyl | F | F | F | F |
| I-754 | 4-isopropyloxycarbonylamino-cinnamyl | F | F | F | F |
| I-755 | 3-naphthalen-2-yl-allyl | F | F | F | F |
| I-756 | 3-(5-trifluoromethyl-pyridin-2-yl)-allyl | F | F | F | F |
| I-757 | 3-(5-chloro-pyridin-2-yl)-allyl | F | F | F | F |
| I-758 | 3-pyridin-4-yl-allyl | F | F | F | F |
| I-759 | 3-(2-Chloro-pyridin-4-yl)-allyl | F | F | F | F |
| I-760 | 4-chlorobenzyl | H | F | H | F |
| I-761 | Cinnamyl | H | F | H | F |
| I-762 | 4-chlorocinnamyl | H | F | H | F |
| I-763 | 4-fluorocinnamyl | H | F | H | F |
| I-764 | 4-bromocinnamyl | H | F | H | F |
| I-765 | 4-trifluoromethylcinnamyl | H | F | H | F |

TABLE 1-continued

| Compound No | R⁸ | Rᵃ | Rᵇ | Rᶜ | Rᵈ |
|---|---|---|---|---|---|
| I-766 | 4-trifluoromethoxycinnamyl | H | F | H | F |
| I-767 | 4-pentafluoroethoxycinnamyl | H | F | H | F |
| I-768 | 4-methoxycinnamyl | H | F | H | F |
| I-769 | 4-ethoxycinnamyl | H | F | H | F |
| I-770 | 4-cyanocinnamyl | H | F | H | F |
| I-771 | 3-(6-chloro-pyridin-3-yl)-allyl | H | F | H | F |
| I-772 | 3-(4-chlorophenyl)-but-2-enyl | H | F | H | F |
| I-773 | 3-(4-chlorophenyl)-3-fluoro-allyl | H | F | H | F |
| I-774 | 3-chloro-4-fluoro-cinnamyl | H | F | H | F |
| I-775 | 3,5-dichloro-cinnamyl | H | F | H | F |
| I-776 | 5-phenyl-penta-2,4-dienyl | H | F | H | F |
| I-777 | 4-isopropyloxycarbonylamino-cinnamyl | H | F | H | F |
| I-778 | 3-naphthalen-2-yl-allyl | H | F | H | F |
| I-779 | 3-(5-trifluoromethyl-pyridin-2-yl)-allyl | H | F | H | F |
| I-780 | 3-(5-chloro-pyridin-2-yl)-allyl | H | F | H | F |
| I-781 | 3-pyridin-4-yl-allyl | H | F | H | F |
| I-782 | 3-(2-Chloro-pyridin-4-yl)-allyl | H | F | H | F |
| I-783 | 4-chlorobenzyl | H | F | F | H |
| I-784 | Cinnamyl | H | F | F | H |
| I-785 | 4-chlorocinnamyl | H | F | F | H |
| I-786 | 4-fluorocinnamyl | H | F | F | H |
| I-787 | 4-bromocinnamyl | H | F | F | H |
| I-788 | 4-trifluoromethylcinnamyl | H | F | F | H |
| I-789 | 4-trifluoromethoxycinnamyl | H | F | F | H |
| I-790 | 4-pentafluoroethoxycinnamyl | H | F | F | H |
| I-791 | 4-methoxycinnamyl | H | F | F | H |
| I-792 | 4-ethoxycinnamyl | H | F | F | H |
| I-793 | 4-cyanocinnamyl | H | F | F | H |
| I-794 | 3-(6-chloro-pyridin-3-yl)-allyl | H | F | F | H |
| I-795 | 3-(4-chlorophenyl)-but-2-enyl | H | F | F | H |
| I-796 | 3-(4-chlorophenyl)-3-fluoro-allyl | H | F | F | H |
| I-797 | 3-chloro-4-fluoro-cinnamyl | H | F | F | H |
| I-798 | 3,5-dichloro-cinnamyl | H | F | F | H |
| I-799 | 5-phenyl-penta-2,4-dienyl | H | F | F | H |
| I-800 | 4-isopropyloxycarbonylamino-cinnamyl | H | F | F | H |
| I-801 | 3-naphthalen-2-yl-allyl | H | F | F | H |
| I-802 | 3-(5-trifluoromethyl-pyridin-2-yl)-allyl | H | F | F | H |
| I-803 | 3-(5-chloro-pyridin-2-yl)-allyl | H | F | F | H |
| I-804 | 3-pyridin-4-yl-allyl | H | F | F | H |
| I-805 | 3-(2-Chloro-pyridin-4-yl)-allyl | H | F | F | H |
| I-806 | 4-chlorobenzyl | H | F | F | H |
| I-807 | Cinnamyl | H | H | F | F |
| I-808 | 4-chlorocinnamyl | H | H | F | F |
| I-809 | 4-fluorocinnamyl | H | H | F | F |
| I-810 | 4-bromocinnamyl | H | H | F | F |
| I-811 | 4-trifluoromethylcinnamyl | H | H | F | F |
| I-812 | 4-trifluoromethoxycinnamyl | H | H | F | F |
| I-813 | 4-pentafluoroethoxycinnamyl | H | H | F | F |
| I-814 | 4-methoxycinnamyl | H | H | F | F |
| I-815 | 4-ethoxycinnamyl | H | H | F | F |
| I-816 | 4-cyanocinnamyl | H | H | F | F |
| I-817 | 3-(6-chloro-pyridin-3-yl)-allyl | H | H | F | F |
| I-818 | 3-(4-chlorophenyl)-but-2-enyl | H | H | F | F |
| I-819 | 3-(4-chlorophenyl)-3-fluoro-allyl | H | H | F | F |
| I-820 | 3-chloro-4-fluoro-cinnamyl | H | H | F | F |
| I-821 | 3,5-dichloro-cinnamyl | H | H | F | F |
| I-822 | 5-phenyl-penta-2,4-dienyl | H | H | F | F |
| I-823 | 4-isopropyloxycarbonylamino-cinnamyl | H | H | F | F |
| I-824 | 3-naphthalen-2-yl-allyl | H | H | F | F |
| I-825 | 3-(5-trifluoromethyl-pyridin-2-yl)-allyl | H | H | F | F |
| I-826 | 3-(5-chloro-pyridin-2-yl)-allyl | H | H | F | F |
| I-827 | 3-pyridin-4-yl-allyl | H | H | F | F |
| I-828 | 3-(2-Chloro-pyridin-4-yl)-allyl | H | H | F | F |
| I-829 | 4-chlorobenzyl | H | H | Cl | Cl |
| I-830 | Cinnamyl | H | H | Cl | Cl |
| I-831 | 4-chlorocinnamyl | H | H | Cl | Cl |
| I-832 | 4-fluorocinnamyl | H | H | Cl | Cl |
| I-833 | 4-bromocinnamyl | H | H | Cl | Cl |
| I-834 | 4-trifluoromethylcinnamyl | H | H | Cl | Cl |
| I-835 | 4-trifluoromethoxycinnamyl | H | H | Cl | Cl |
| I-836 | 4-pentafluoroethoxycinnamyl | H | H | Cl | Cl |
| I-837 | 4-methoxycinnamyl | H | H | Cl | Cl |
| I-838 | 4-ethoxycinnamyl | H | H | Cl | Cl |
| I-839 | 4-cyanocinnamyl | H | H | Cl | Cl |
| I-840 | 3-(6-chloro-pyridin-3-yl)-allyl | H | H | Cl | Cl |
| I-841 | 3-(4-chlorophenyl)-but-2-enyl | H | H | Cl | Cl |
| I-842 | 3-(4-chlorophenyl)-3-fluoro-allyl | H | H | Cl | Cl |
| I-843 | 3-chloro-4-fluoro-cinnamyl | H | H | Cl | Cl |
| I-844 | 3,5-dichloro-cinnamyl | H | H | Cl | Cl |
| I-845 | 5-phenyl-penta-2,4-dienyl | H | H | Cl | Cl |
| I-846 | 4-isopropyloxycarbonylamino-cinnamyl | H | H | Cl | Cl |
| I-847 | 3-naphthalen-2-yl-allyl | H | H | Cl | Cl |
| I-848 | 3-(5-trifluoromethyl-pyridin-2-yl)-allyl | H | H | Cl | Cl |
| I-849 | 3-(5-chloro-pyridin-2-yl)-allyl | H | H | Cl | Cl |
| I-850 | 3-pyridin-4-yl-allyl | H | H | Cl | Cl |
| I-851 | 3-(2-Chloro-pyridin-4-yl)-allyl | H | H | Cl | Cl |
| I-852 | 4-chlorobenzyl | H | Cl | Cl | H |
| I-853 | Cinnamyl | H | Cl | Cl | H |
| I-854 | 4-chlorocinnamyl | H | Cl | Cl | H |
| I-855 | 4-fluorocinnamyl | H | Cl | Cl | H |
| I-856 | 4-bromocinnamyl | H | Cl | Cl | H |
| I-857 | 4-trifluoromethylcinnamyl | H | Cl | Cl | H |
| I-858 | 4-trifluoromethoxycinnamyl | H | Cl | Cl | H |
| I-859 | 4-pentafluoroethoxycinnamyl | H | Cl | Cl | H |
| I-860 | 4-methoxycinnamyl | H | Cl | Cl | H |
| I-861 | 4-ethoxycinnamyl | H | Cl | Cl | H |
| I-862 | 4-cyanocinnamyl | H | Cl | Cl | H |
| I-863 | 3-(6-chloro-pyridin-3-yl)-allyl | H | Cl | Cl | H |
| I-864 | 3-(4-chlorophenyl)-but-2-enyl | H | Cl | Cl | H |
| I-865 | 3-(4-chlorophenyl)-3-fluoro-allyl | H | Cl | Cl | H |
| I-866 | 3-chloro-4-fluoro-cinnamyl | H | Cl | Cl | H |
| I-867 | 3,5-dichloro-cinnamyl | H | Cl | Cl | H |
| I-868 | 5-phenyl-penta-2,4-dienyl | H | Cl | Cl | H |
| I-869 | 4-isopropyloxycarbonylamino-cinnamyl | H | Cl | Cl | H |
| I-870 | 3-naphthalen-2-yl-allyl | H | Cl | Cl | H |
| I-871 | 3-(5-trifluoromethyl-pyridin-2-yl)-allyl | H | Cl | Cl | H |
| I-872 | 3-(5-chloro-pyridin-2-yl)-allyl | H | Cl | Cl | H |
| I-873 | 3-pyridin-4-yl-allyl | H | Cl | Cl | H |
| I-874 | 3-(2-Chloro-pyridin-4-yl)-allyl | H | Cl | Cl | H |
| I-875 | 4-chlorobenzyl | H | Cl | H | Cl |
| I-876 | Cinnamyl | H | Cl | H | Cl |
| I-877 | 4-chlorocinnamyl | H | Cl | H | Cl |
| I-878 | 4-fluorocinnamyl | H | Cl | H | Cl |
| I-879 | 4-bromocinnamyl | H | Cl | H | Cl |
| I-880 | 4-trifluoromethylcinnamyl | H | Cl | H | Cl |
| I-881 | 4-trifluoromethoxycinnamyl | H | Cl | H | Cl |
| I-882 | 4-pentafluoroethoxycinnamyl | H | Cl | H | Cl |
| I-883 | 4-methoxycinnamyl | H | Cl | H | Cl |
| I-884 | 4-ethoxycinnamyl | H | Cl | H | Cl |
| I-885 | 4-cyanocinnamyl | H | Cl | H | Cl |
| I-886 | 3-(6-chloro-pyridin-3-yl)-allyl | H | Cl | H | Cl |
| I-887 | 3-(4-chlorophenyl)-but-2-enyl | H | Cl | H | Cl |
| I-888 | 3-(4-chlorophenyl)-3-fluoro-allyl | H | Cl | H | Cl |
| I-889 | 3-chloro-4-fluoro-cinnamyl | H | Cl | H | Cl |
| I-890 | 3,5-dichloro-cinnamyl | H | Cl | H | Cl |
| I-891 | 5-phenyl-penta-2,4-dienyl | H | Cl | H | Cl |
| I-892 | 4-isopropyloxycarbonylamino-cinnamyl | H | Cl | H | Cl |
| I-893 | 3-naphthalen-2-yl-allyl | H | Cl | H | Cl |
| I-894 | 3-(5-trifluoromethyl-pyridin-2-yl)-allyl | H | Cl | H | Cl |
| I-895 | 3-(5-chloro-pyridin-2-yl)-allyl | H | Cl | H | Cl |
| I-896 | 3-pyridin-4-yl-allyl | H | Cl | H | Cl |
| I-897 | 3-(2-Chloro-pyridin-4-yl)-allyl | H | Cl | H | Cl |
| I-898 | 4-chlorocinnamyl | H | CF₃ | H | H |
| I-899 | 4-bromocinnamyl | H | CF₃ | H | H |
| I-900 | 4-trifluoromethylcinnamyl | H | CF₃ | H | H |
| I-901 | 4-trifluoromethoxycinnamyl | H | CF₃ | H | H |

TABLE 1-continued

| Compound No | R⁸ | $R^a$ | $R^b$ | $R^c$ | $R^d$ |
|---|---|---|---|---|---|
| I-902 | 4-chlorocinnamyl | H | H | CF₃ | H |
| I-903 | 4-bromocinnamyl | H | H | CF₃ | H |
| I-904 | 4-trifluoromethylcinnamyl | H | H | CF₃ | H |
| I-905 | 4-trifluoromethoxycinnamyl | H | H | CF₃ | H |
| I-906 | 4-chlorocinnamyl | H | OCF₃ | H | H |
| I-907 | 4-bromocinnamyl | H | OCF₃ | H | H |
| I-908 | 4-trifluoromethylcinnamyl | H | OCF₃ | H | H |
| I-909 | 4-trifluoromethoxycinnamyl | H | OCF₃ | H | H |
| I-910 | 4-chlorocinnamyl | H | H | OCF₃ | H |
| I-911 | 4-bromocinnamyl | H | H | OCF₃ | H |
| I-912 | 4-trifluoromethylcinnamyl | H | H | OCF₃ | H |
| I-913 | 4-trifluoromethoxycinnamyl | H | H | OCF₃ | H |

Table II provides 913 compounds of formula Ib

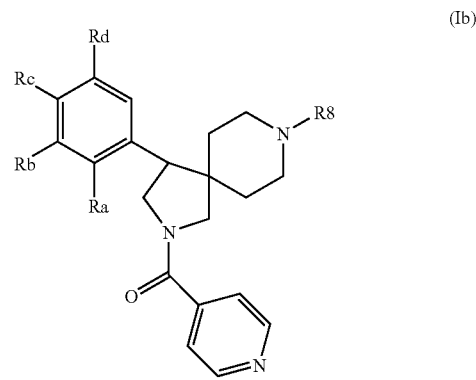
(Ib)

wherein the values of $R^8$, $R^a$, $R^b$, $R^c$ and $R^d$ are given in Table 1.

Table III provides 913 compounds of formula Ic

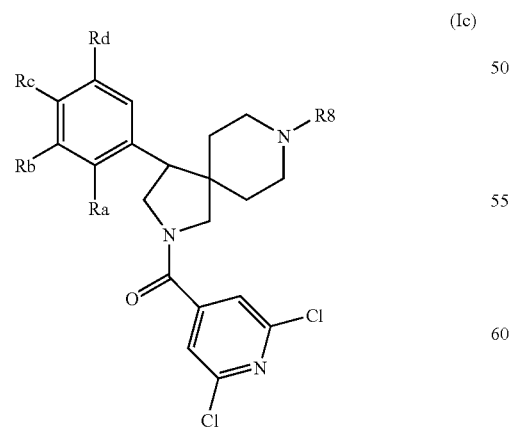
(Ic)

wherein the values of $R^8$, $R^a$, $R^b$, $R^c$ and $R^d$ are given in Table 1.

Table IV provides 913 compounds of formula Id

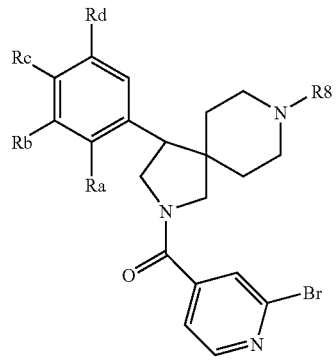
(Id)

wherein the values of $R^8$, $R^a$, $R^b$, $R^c$ and $R^d$ are given in Table 1.

Table V provides 913 compounds of formula Ie

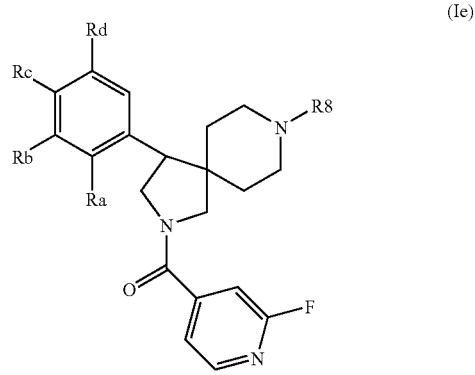
(Ie)

wherein the values of $R^8$, $R^a$, $R^b$, $R^c$ and $R^d$ are given in Table 1.

Table VI provides 913 compounds of formula If

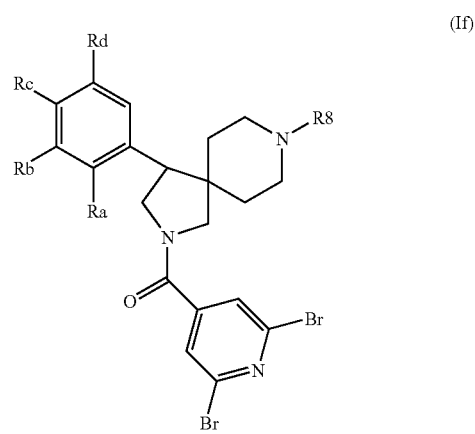
(If)

wherein the values of $R^8$, $R^a$, $R^b$, $R^c$ and $R^d$ are given in Table 1.

Table VII provides 913 compounds of formula Ig

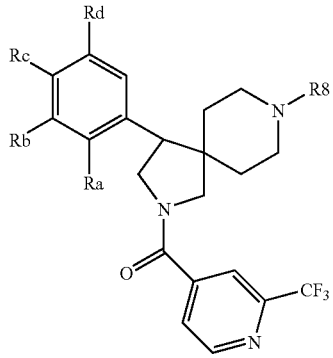

wherein the values of $R^8$, $R^a$, $R^b$, $R^c$ and $R^d$ are given in Table 1.

Table VIII provides 913 compounds of formula Ih

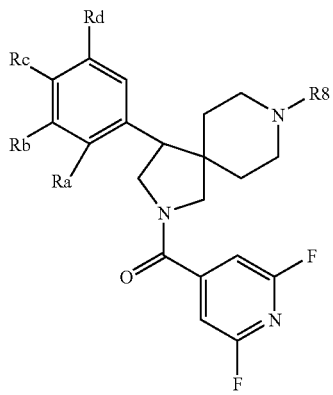

wherein the values of $R^8$, $R^a$, $R^b$, $R^c$ and $R^d$ are given in Table 1.

Table IX provides 913 compounds of formula Ii

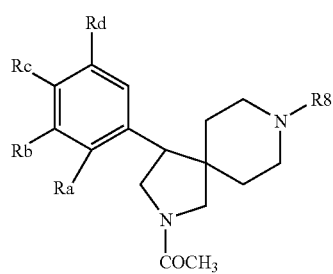

wherein the values of $R^8$, $R^a$, $R^b$, $R^c$ and $R^d$ are given in Table 1.

Table X provides 913 compounds of formula Ij

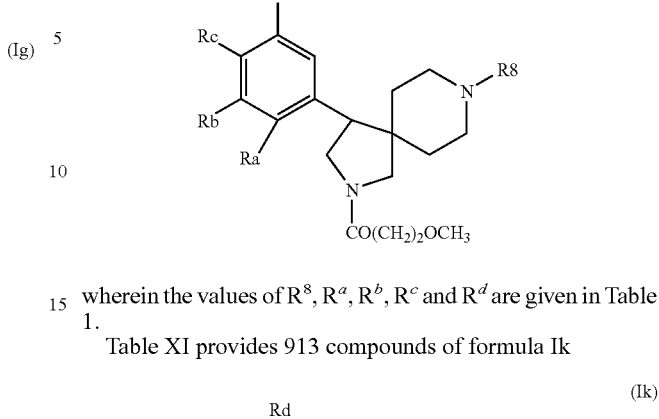

wherein the values of $R^8$, $R^a$, $R^b$, $R^c$ and $R^d$ are given in Table 1.

Table XI provides 913 compounds of formula Ik

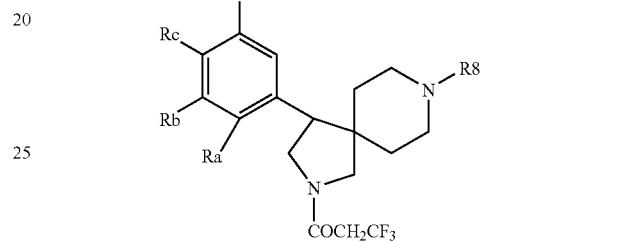

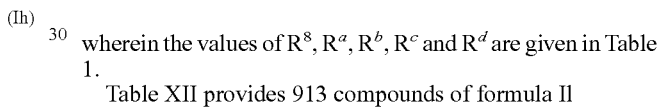

wherein the values of $R^8$, $R^a$, $R^b$, $R^c$ and $R^d$ are given in Table 1.

Table XII provides 913 compounds of formula Il

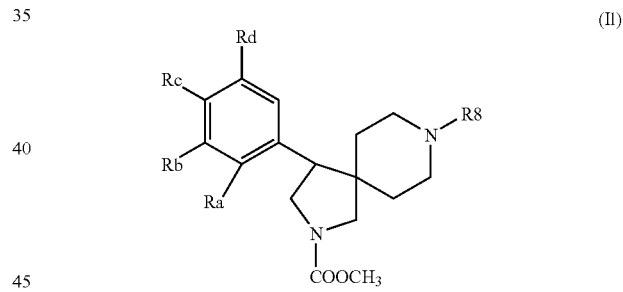

wherein the values of $R^8$, $R^a$, $R^b$, $R^c$ and $R^d$ are given in Table 1.

Table XIII provides 913 compounds of formula Im

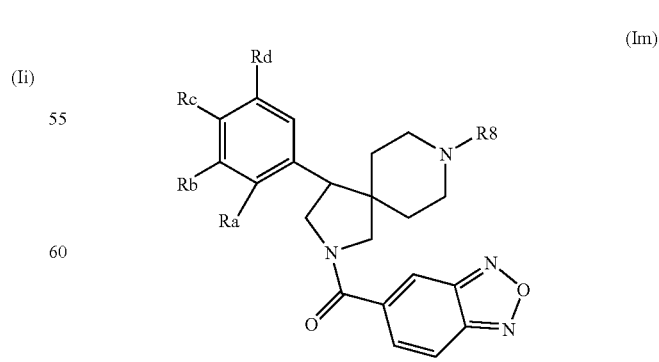

wherein the values of $R^8$, $R^a$, $R^b$, $R^c$ and $R^d$ are given in Table 1.

Table XIV provides 913 compounds of formula In

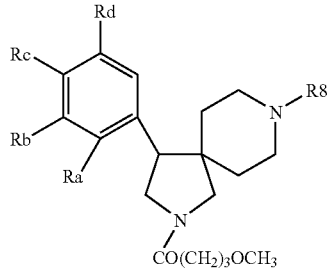

wherein the values of $R^8$, $R^a$, $R^b$, $R^c$ and $R^d$ are given in Table 1.

Table XV provides 913 compounds of formula Io

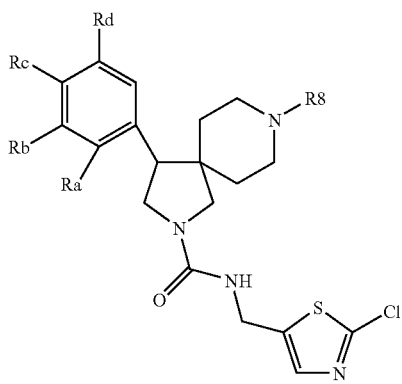

wherein the values of $R^8$, $R^a$, $R^b$, $R^c$ and $R^d$ are given in Table 1.

Table XVI provides 913 compounds of formula Ip

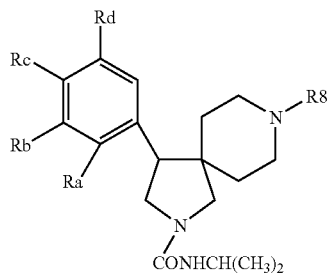

wherein the values of $R^8$, $R^a$, $R^b$, $R^c$ and $R^d$ are given in Table 1.

Table XVII provides 913 compounds of formula Iq

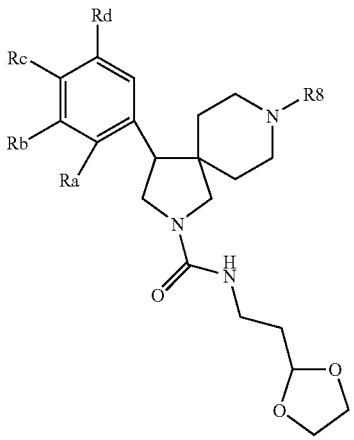

wherein the values of $R^8$, $R^a$, $R^b$, $R^c$ and $R^d$ are given in Table 1.

Table XVIII provides 913 compounds of formula Ir

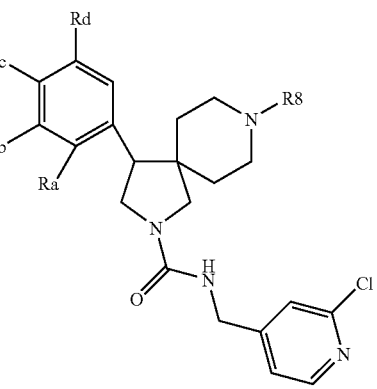

wherein the values of $R^8$, $R^a$, $R^b$, $R^c$ and $R^d$ are given in Table 1.

Table XIX provides 913 compounds of formula Is

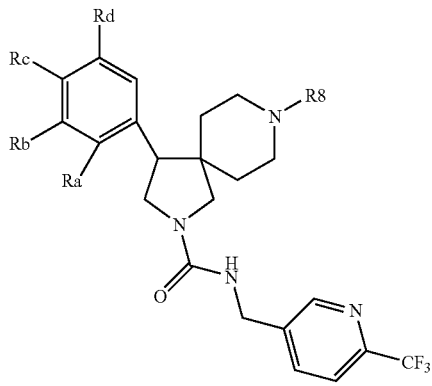

wherein the values of $R^8$, $R^a$, $R^b$, $R^c$ and $R^d$ are given in Table 1.

Table XX provides 913 compounds of formula It

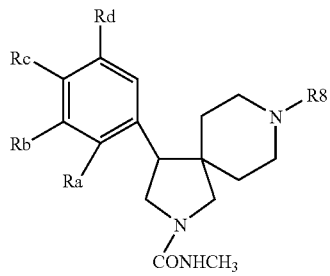
(It)

wherein the values of $R^8$, $R^a$, $R^b$, $R^c$ and $R^d$ are given in Table 1.

Table XXI provides 913 compounds of formula Iu

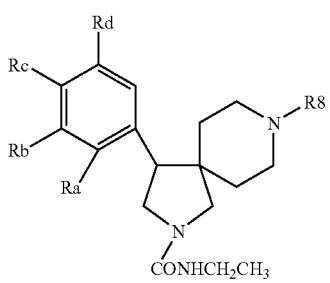
(Iu)

wherein the values of $R^8$, $R^a$, $R^b$, $R^c$ and $R^d$ are given in Table 1.

Table XXII provides 913 compounds of formula Iv

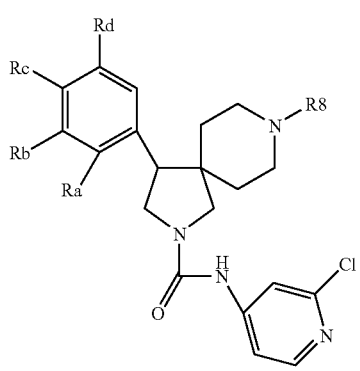
(Iv)

wherein the values of $R^8$, $R^a$, $R^b$, $R^c$ and $R^d$ are given in Table 1.

Table XXIII provides 913 compounds of formula Iw

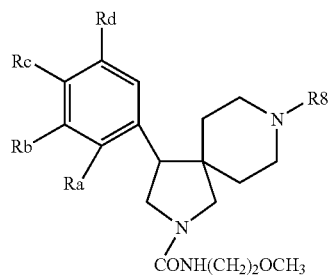
(Iw)

wherein the values of $R^8$, $R^a$, $R^b$, $R^c$ and $R^d$ are given in Table 1.

Table XXIV provides 913 compounds of formula Ix

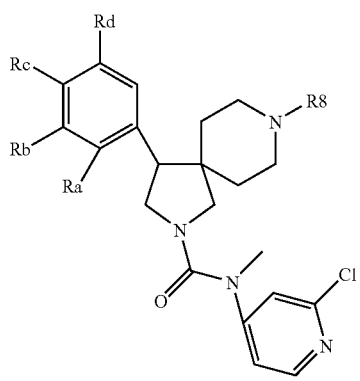
(Ix)

wherein the values of $R^8$, $R^a$, $R^b$, $R^c$ and $R^d$ are given in Table 1.

Table XXV provides 913 compounds of formula Iy

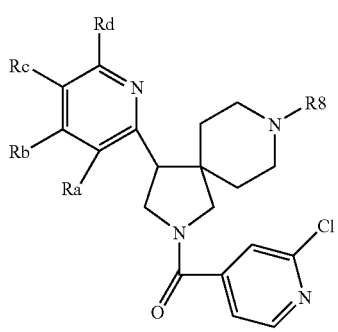
(Iy)

wherein the values of $R^8$, $R^a$, $R^b$, $R^c$ and $R^d$ are given in Table 1.

The compounds of the invention may be made by a variety of methods.

For example compounds of the general formula I may be prepared according to the reactions of Scheme 1.

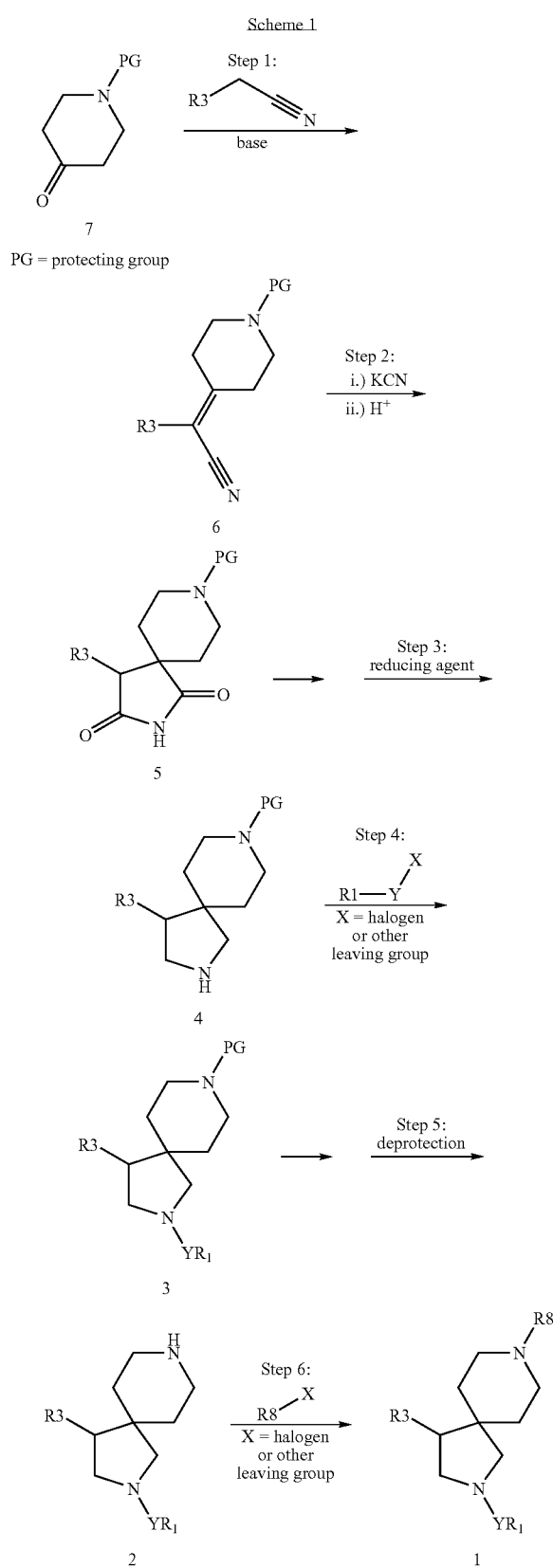

PG is R[8] or is a suitable protective group for example a group such as BOC, benzyl or alkyl.

Thus a compound of formula 1 may be obtained from a compound of formula 2 by reaction with a suitable reagent R[8]—X, wherein R[8] has the same meaning as in formula 1 and X is a halogen or other leaving group. Such a reagent R[8]—X may be, for example, an alkylhalide, an acid chloride, or an anhydride of a carboxylic acid. Alternatively, some compounds of formula 1 may be obtained from a compound of formula 2 by reaction with an aldehyde or ketone and a reducing agent, such as, for example, sodium cyanoborohydride or sodium triacetoxyborohydride. Suitable methods for obtaining a compound of the formula 1 from a compound of the formula 2 are known to a person skilled in the art.

Compounds of formula 2 may be prepared from compounds of formula 3 by cleavage of the protecting group, according to methods which are known to a person skilled in the art.

Compounds of formula 3 may be obtained from compounds of formula 4 by reaction with a suitable reagent R[1]—Y—X, wherein R[1] and Y have the same meaning as in formula 1 and X is a halogen or other leaving group. Such a reagent R[1]—Y—X may be, for example, an alkylhalide, an acid chloride, or an anhydride of a carboxylic acid or sulfonic acid. Alternatively, some compounds of formula 3 may be obtained from a compound of formula 4 by reaction with an isocyanate or isothiocyanate. Suitable methods for obtaining a compound of the formula 3 from a compound of the formula 4 are known to a person skilled in the art.

Compounds of formula 4 may be prepared from compounds of formula 5 by reaction with a reducing agent, such as, for example, lithium borohydride or borane. Suitable reducing agents for this reaction are known to a person skilled in the art.

Compounds of formula 5 may be prepared from compounds of formula 6 by reaction with a cyanide source, such as, for example, sodium cyanide or potassium cyanide, followed by treatment with an acid, such as, for example, hydrochloric acid. Such a reaction has been described in: *Bull. Soc. China. Belg.* 1981, 90, (7), 757-765.

Compounds of formula 6 may be prepared from compounds of formula 7 by reaction with a suitable reagent R[3]—CH$_2$—CN, wherein R[3] has the same meaning as in formula 1. This reaction is carried out in the presence of a suitable base, such as, for example, sodium ethoxide. Suitable bases for this reaction are known to a person skilled in the art.

Compounds of formula 7 are known or may be made from known compounds by known methods.

Certain compounds of formula 2, formula 3, formula 4, formula 5 and formula 6 are novel and as such form a further aspect of the invention.

Instead of the BOC group other suitable protective groups may be used. Suitable protective groups are known to a person skilled in the art. Such protective groups have been described, for example, in: Protective Groups in Organic Synthesis, 2nd Ed., Greene, Theodora W.; Wuts, Peter G. M.; 1991, John Wiley and Sons, Inc., New York.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollwowi), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus*, and *R. santonensis*) and the *Termitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water to soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R, 3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, Spiromesifen; or s) Flubendiamid or bromo-N-[4-chloro-2-methyl-6-[(methylamino)carbonyl]phenyl]-1-(3-chloro-2-pyridinyl)-1H-pyrazole-5-carboxamide.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, trifluinizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

EXAMPLE 1

This Example Describes the Preparation of 8-[(E)-3-(4-Chloro-phenyl)-allyl]-4-(4-fluorophenyl)-2,8-diaza-spiro[4.5]dec-2-yl]-(2-chloro-pyridin-4-yl)-methanone Steps 1-3 were performed in analogy to the procedures described for an unsubstituted phenyl-analogue; cf. Bull. Soc. Chim. Belg. 1981, 90, (7), 757-765.

Step 1: (1-Benzyl-piperidin-4-ylidene)-(4-fluoro-phenyl)-acetonitrile (4-Fluoro-phenyl)-acetonitrile (28.4 ml) is added to a solution of sodium ethoxide (14.3 g) in ethanol (230 ml), followed by the addition of 1-benzyl-piperidin-4-one (28.2 ml). The mixture is heated on reflux for 3 hours. After cooling to room temperature, the ethanol is evaporated, and the residue is extracted with ethyl acetate and water. The organic phase is washed with brine, dried over sodium sulfate and the solvent evaporated. The crude product is purified by crystallisation from ethanol, yielding (1-benzyl-piperidin-4-ylidene)-(4-fluorophenyl)-acetonitrile, mp. 81-83° C. A second batch of this product is obtained by evaporation of the mother liquor, followed by chromatography on silica gel, using hexane and ethyl acetate (4:1) as eluent.

Step 2: 8-Benzyl-4-(4-fluoro-phenyl)-2,8-diaza-spiro[4.5]decane-1,3-dione

A solution of (1-benzyl-piperidin-4-ylidene)-(4-fluoro-phenyl)-acetonitrile (15.3 g) in ethanol (100 ml) is heated to 50° C. At this temperature, a solution of potassium cyanide (3.9 g) in water (10 ml) is added. Subsequently, the mixture is heated to reflux for 3 days. Then the ethanol is distilled off, to the residue is added water (75 ml), then hydrochloric acid (36%, 75 ml). This mixture is heated to 95° C. for 2 days. After cooling to room temperature, the mixture is cooled in an ice bath and sodium hydroxide (4N solution in water) is slowly added until the pH is in the range of 7-8. The resulting solid is filtered, triturated with ethyl acetate, and washed with diethylether. The product so obtained is used for step 3 without further purification.

Step 3: 8-Benzyl-4-(4-fluoro-phenyl)-2,8-diaza-spino[4.5]decane

Lithium aluminiumhydride (1.14 g) is suspended in dry tetrahydrofuran at room temperature under an atmosphere of nitrogen. 8-Benzyl-4-(4-fluoro-phenyl)-2,8-diaza-spiro[4.5]decane-1,3-dione (3.5 g) is added in portions over a period of 30 minutes. The resulting suspension is heated to 60° C. and stirred at this temperature for 3 days. Then the mixture is cooled to 0° C. and water (10 ml) is added slowly. The mixture is stirred at 0° C. for one hour, then filtered, and the solution is extracted with ethyl acetate. The organic phase is washed with brine, dried over sodium sulfate and evaporated. Crude 8-benzyl-4-(4-fluoro-phenyl)-2,8-diaza-spiro[4.5]decane so obtained is used for step 4 without further purification.

Step 4: [8-Benzyl-4-(4-fluoro-phenyl)-2,8-diaza-spiro[4.5]dec-2-yl]-(2-chloro-pyridin-4-yl)-methanone 8-Benzyl-4-(4-fluoro-phenyl)-2,8-diaza-spiro[4.5]decane (2.7 g) is dissolved in dichloromethane (30 ml). Then triethylamine (1.5 ml) is added, followed by a solution of 2-chloro-isonicotinoyl chloride (2.0 g) in dichloromethane. The mixture is stirred at room temperature for 18 hours, then extracted with aqueous sodium bicarbonate (1 N). The organic phase is separated, washed with brine, dried over sodium sulfate, and evaporated. The crude product is purified by chromatography on silica gel with ethyl acetate and methanol (20:1) as eluent, yielding [8-benzyl-4-(4-fluoro-phenyl)-2,8-diaza-spiro[4.5]dec-2-yl]-(2-chloropyridin-4-yl)-methanone, mp. 70-72° C.

Step 5: (2-Chloro-pyridin-4-yl)-[4-(4-fluoro-phenyl)-2,8-diaza-spiro[4.5]dec-2-yl]-methanone

[8-Benzyl-4-(4-fluoro-phenyl)-2,8-diaza-spiro[4.5]dec-2-yl]-(2-chloro-pyridin-4-yl)-methanone (1.0 g) is dissolved in toluene (30 ml), then 1-chloroethyl chloroformate (4.3 ml) is added. The mixture is heated to reflux for 2 hours, then cooled to room temperature and extracted with aqueous sodium bicarbonate (1 N). The organic phase is washed with water, dried over sodium sulfate, and evaporated. The residue is dissolved in methanol (30 ml), and stirred at 60° C. for 2 hours. Then the mixture is cooled to room temperature, and the solvent is evaporated. Crude (2-chloro-pyridin-4-yl)-[4-(4-fluoro-phenyl)-2,8-diazaspiro[4.5]dec-2-yl]-methanone so obtained is used for step 6 without further purification.

Step 6: [8-[(E)-3-(4-Chloro-phenyl)-allyl]-4-(4-fluoro-phenyl)-2,8-diaza-spiro[4.5]dec-2-yl]-(2-chloro-pyridin-4-yl)-methanone (2-Chloro-pyridin-4-yl)-[4-(4-fluoro-phenyl)-2,8-diaza-spiro[4.5]dec-2-yl]-methanone (1.7 g) and ethyl-diisopropyl-amine (1.5 ml) are dissolved in acetonitrile (50 ml). 1-chloro-4-((E)-3-chloro-propenyl)-benzene (0.84 g) is added, and the mixture is heated to 70° C. for 6 hours. Then the reaction mixture is cooled to room temperature, and the solvent is evaporated. The crude product is purified by chromatography on silica gel with ethyl acetate and methanol (20:1) as eluent, yielding [8-[(E)-3-(4-chloro-phenyl)-allyl]-4-(4-fluoro-phenyl)-2,8-diazaspiro[4.5]dec-2-yl]-(2-chloro-pyridin-4-yl)-methanone, mp. 79-81° C.

The following compounds were made in an analogous manner.

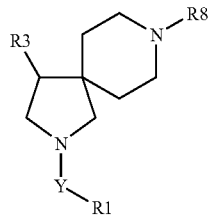

| Compound No | R8 | YR1 | R3 | Retention Time (min) | LC method |
|---|---|---|---|---|---|
| E.1 | (E)-3-(4-chlorophenyl)-allyl | 2-chloro-pyridin-4-yl-carbonyl | 4-chlorophenyl | 2.87 | A |
| E.2 | (E)-3-(4-chlorophenyl)-allyl | 2-chloro-pyridin-4-yl-carbonyl | 4-fluorophenyl | 2.71 | A |

-continued

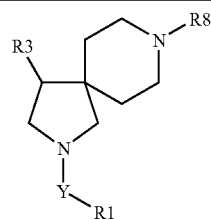

| Compound No | R8 | YR1 | R3 | Retention Time (min) | LC method |
|---|---|---|---|---|---|
| E.3 | (E)-3-(4-bromo-phenyl)-allyl | 2-chloro-pyridin-4-carbonyl | 4-fluoro-phenyl | 1.34 | C |
| E.4 | (E)-3-(4-trifluoromethyl-phenyl)-allyl | 2-chloro-pyridin-4-carbonyl | 4-fluoro-phenyl | 1.39 | B |
| E.5 | (E)-3-(4-trifluoromethoxy-phenyl)-allyl | 2-chloro-pyridin-4-carbonyl | 4-fluoro-phenyl | 1.39 | C |
| E.6 | Benzyl | 2-chloro-pyridine-4-carbonyl | 4-fluoro-phenyl | 2.26 | G |
| E.7 | (4'-fluoro-biphenyl-4-yl)-methyl | 2-chloro-pyridine-4-carbonyl | 4-fluoro-phenyl | 1.40 | F |
| E.8 | (E)-3-(4-chloro-phenyl)-allyl | acetyl | 4-fluoro-phenyl | 1.22 | D |
| E.9 | (E)-3-(4-chloro-phenyl)-allyl | 2,6-dichloro-pyridine-4-carbonyl | 4-fluoro-phenyl | 1.46 | D |
| E.10 | (E)-3-(4-chloro-phenyl)-allyl | 2-fluoro-pyridine-4-carbonyl | 4-fluoro-phenyl | 1.36 | D |
| E.11 | (E)-3-(4-chloro-phenyl)-allyl | 2-chloro-pyridine-4-carbonyl | 6-ethoxy-pyridin-2-yl | 1.34 | F |
| E.12 | (E)-3-(4-chloro-phenyl)-allyl | 2-chloro-pyridine-4-carbonyl | thiophen-2-yl | 1.35 | D |
| E.13 | (E)-3-(4-chloro-phenyl)-allyl | 2-chloro-pyridine-4-carbonyl | thiophen-3-yl | 1.29 | F |
| E.14 | (E)-3-(4-bromo-phenyl)-allyl | 2-chloro-pyridine-4-carbonyl | thiophen-3-yl | 1.31 | F |
| E.15 | (E)-3-(4-chloro-phenyl)-allyl | (2-chloro-thiazol-5-ylmethyl)-carbamoyl | 4-fluoro-phenyl | 1.31 | F |
| E.16 | (E)-3-(4-chloro-phenyl)-allyl | (6-trifluoromethyl-pyridin-3-ylmethyl)-carbamoyl | 4-fluoro-phenyl | 1.37 | D |
| E.17 | (E)-3-(4-bromo-phenyl)-allyl | 2-chloro-pyridin-4-carbonyl | 2-trifluoromethoxy-phenyl | 1.42 | F |
| E.18 | (E)-3-(4-chloro-phenyl)-allyl | 2-chloro-pyridin-4-carbonyl | 2-trifluoromethoxy-phenyl | 1.39 | F |

-continued

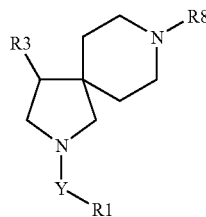

| Compound No | R8 | YR1 | R3 | Retention Time (min) | LC method |
|---|---|---|---|---|---|
| E.19 | (E)-3-(4-trifluoromethyl-phenyl)-allyl | 2-chloro-pyridine-4-carbonyl | 2-trifluoromethoxy-phenyl | 1.47 | D |
| E.20 | (E)-3-(4-trifluoromethoxy-phenyl)-allyl | 2-chloro-pyridine-4-carbonyl | 2-trifluoromethoxy-phenyl | 1.50 | D |
| E.21 | (E)-3-(4-chloro-phenyl)-allyl | 2-chloro-pyridine-4-carbonyl | 2-fluoro-phenyl | 1.31 | D |
| E.22 | (E)-3-(4-chloro-phenyl)-allyl | 2-chloro-pyridine-4-carbonyl | phenyl | 1.30 | D |
| E.23 | (E)-3-(4-chloro-phenyl)-allyl | 2-chloro-pyridine-4-carbonyl | 2,4-difluoro-phenyl | 1.34 | D |
| E.24 | (E)-3-(4-chloro-phenyl)-allyl | 2-chloro-pyridine-4-carbonyl | 2,6-difluoro-phenyl | 1.32 | D |
| E.25 | (E)-3-(4-chloro-phenyl)-allyl | 2-chloro-pyridine-4-carbonyl | 2,5-difluoro-phenyl | 1.34 | D |
| E.26 | (E)-3-(4-chloro-phenyl)-allyl | 2-chloro-pyridine-4-carbonyl | 3,4-difluoro-phenyl | 1.35 | D |
| E.27 | Benzyl | 2-chloro-pyridine-4-carbonyl | 2,4-difluoro-phenyl | 1.16 | D |
| E.28 | 3-methyl-butyl | 2-chloro-pyridine-4-carbonyl | 4-fluoro-phenyl | 0.97 | E |
| E.29 | cyclohexyl-methyl | 2-chloro-pyridine-4-carbonyl | 4-fluoro-phenyl | 1.08 | E |
| E.30 | (1-methyl-1H-imidazol-2-yl)-methyl | 2-chloro-pyridine-4-carbonyl | 4-fluoro-phenyl | 0.80 | E |
| E.31 | 4-isopropyl-benzyl | 2-chloro-pyridine-4-carbonyl | 4-fluoro-phenyl | 1.25 | E |
| E.32 | 2-phenyl-propyl | 2-chloro-pyridine-4-carbonyl | 4-fluoro-phenyl | 1.06 | E |
| E.33 | (4-chloro-1-methyl-1H-pyrazol-3-yl)-methyl | 2-chloro-pyridine-4-carbonyl | 4-fluoro-phenyl | 0.87 | E |
| E.34 | (2,3-dihydro-benzofuran-5-yl)-methyl | 2-chloro-pyridine-4-carbonyl | 4-fluoro-phenyl | 1.00 | E |
| E.35 | (5-methylsulfanyl-thiophen-2-yl)-methyl | 2-chloro-pyridine-4-carbonyl | 4-fluoro-phenyl | 1.08 | E |
| E.36 | (6-methoxy-pyridin-3-yl)-methyl | 2-chloro-pyridine-4-carbonyl | 4-fluoro-phenyl | 0.88 | E |
| E.37 | (E)-3-phenyl-allyl | 2-chloro-pyridine-4-carbonyl | 4-fluoro-phenyl | 1.11 | E |
| E.38 | 4-ethoxy-benzyl | 2-chloro-pyridine-4-carbonyl | 4-fluoro-phenyl | 1.09 | E |
| E.39 | (E)-3-(4-methoxy-phenyl)-allyl | 2-chloro-pyridine-4-carbonyl | 4-fluoro-phenyl | 1.10 | E |

-continued

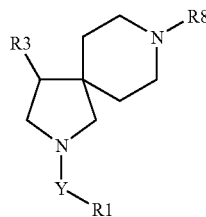

| Compound No | R8 | YR1 | R3 | Retention Time (min) | LC method |
|---|---|---|---|---|---|
| E.40 | 5-chloro-2-hydroxy-benzyl | 2-chloro-pyridine-4-carbonyl | 4-fluoro-phenyl | 1.04 | E |
| E.41 | 4-borono-2-fluoro-benzyl | 2-chloro-pyridine-4-carbonyl | 4-fluoro-phenyl | 0.84 | E |
| E.42 | (6-methoxy-naphthalen-2-yl)-methyl | 2-chloro-pyridin-4-carbonyl | 4-fluoro-phenyl | 1.19 | E |
| E.43 | 2-(2-nitro-phenyl)-allyl | 2-chloro-pyridine-4-carbonyl | 4-fluoro-phenyl | 1.10 | E |
| E.44 | (4-methyl-2-phenyl-pyrimidin-5-yl)-methyl | 2-chloro-pyridine-4-carbonyl | 4-fluoro-phenyl | 1.20 | E |
| E.45 | (4-chloro-6-fluoro-2H-chromen-3-yl)-methyl | 2-chloro-pyridine-4-carbonyl | 4-fluoro-phenyl | 1.20 | E |
| E.46 | 4-trifluoromethoxy-benzyl | 2-chloro-pyridine-4-carbonyl | 4-fluoro-phenyl | 1.20 | E |
| E.47 | 4-pyridin-2-yl-benzyl | 2-chloro-pyridine-4-carbonyl | 4-fluoro-phenyl | 0.94 | E |
| E.48 | (5-methyl-1-phenyl-1H-pyrazol-4-yl)-methyl | 2-chloro-pyridine-4-carbonyl | 4-fluoro-phenyl | 1.06 | E |
| E.49 | 4,5-dimethoxy-2-nitro-benzyl | 2-chloro-pyridine-4-carbonyl | 4-fluoro-phenyl | 1.00 | E |
| E.50 | (5-pyridin-2-yl-thiophen-2-yl)-methyl | 2-chloro-pyridine-4-carbonyl | 4-fluoro-phenyl | 1.05 | E |
| E.51 | 5-bromo-2-hydroxy-benzyl | 2-chloro-pyridine-4-carbonyl | 4-fluoro-phenyl | 1.08 | E |
| E.52 | (E)-3-ethoxycarbonyl-allyl | 2-chloro-pyridine-4-carbonyl | 4-fluoro-phenyl | 0.91 | E |
| E.53 | 3-methoxy-benzyl | 2-chloro-pyridine-4-carbonyl | 4-fluoro-phenyl | 1.03 | E |
| E.54 | 2-(2,5,5-trimethyl-[1,3]dioxan-2-yl)-ethyl | 2-chloro-pyridine-4-carbonyl | 4-fluoro-phenyl | 1.10 | E |
| E.55 | (6-chloro-4H-benzo[1,3]dioxin-8-yl)-methyl | 2-chloro-pyridine-4-carbonyl | 4-fluoro-phenyl | 1.10 | E |
| E.56 | 2-phenoxy-ethyl | 2-chloro-pyridine-4-carbonyl | 4-fluoro-phenyl | 1.10 | E |
| E.57 | 2-benzyloxy-ethyl | 2-chloro-pyridine-4-carbonyl | 4-fluoro-phenyl | 1.10 | E |
| E.58 | 2,3-dihydro-benzo[1,4]dioxin-2-yl | 2-chloro-pyridin-4-carbonyl | 4-fluoro-phenyl | 1.09 | E |
| E.59 | biphenyl-4-yl-methyl | 2-chloro-pyridine-4-carbonyl | 4-fluoro-phenyl | 1.29 | E |
| E.60 | 8-(1,3-dioxo-1,3-dihydro-isoindol-2-yl)-octyl | 2-chloro-pyridine-4-carbonyl | 4-fluoro-phenyl | 1.32 | E |

-continued

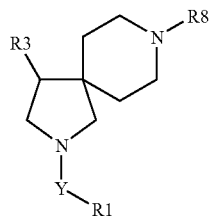

| Compound No | R8 | YR1 | R3 | Retention Time (min) | LC method |
|---|---|---|---|---|---|
| E.61 | 2-[2-(4-chloro-phenyl)-4-methyl-thiazol-5-yl]-2-oxo-ethyl | 2-chloro-pyridine-4-carbonyl | 4-fluoro-phenyl | 1.40 | E |
| E.62 | but-2-ynyl | 2-chloro-pyridine-4-carbonyl | 4-fluoro-phenyl | 0.79 | E |
| E.63 | (E)-3-(4-chloro-phenyl)-allyl | propionyl | 4-fluoro-phenyl | 1.20 | E |
| E.64 | (E)-3-(4-chloro-phenyl)-allyl | cyclohex-3-enecarbonyl | 4-fluoro-phenyl | 1.30 | E |
| E.65 | (E)-3-(4-chloro-phenyl)-allyl | 2,2-dichloro-propionyl | 4-fluoro-phenyl | 1.49 | E |
| E.66 | (E)-3-(4-chloro-phenyl)-allyl | (E)-(3-phenyl-acryloyl) | 4-fluoro-phenyl | 1.40 | E |
| E.67 | (E)-3-(4-chloro-phenyl)-allyl | (E)-3-furan-2-yl-acryloyl | 4-fluoro-phenyl | 1.30 | E |
| E.68 | (E)-3-(4-chloro-phenyl)-allyl | (E)-3-thiophen-2-yl-acryloyl | 4-fluoro-phenyl | 1.40 | E |
| E.69 | (E)-3-(4-chloro-phenyl)-allyl | 2-1H-indol-3-yl-acetyl | 4-fluoro-phenyl | 1.35 | E |
| E.70 | (E)-3-(4-chloro-phenyl)-allyl | (E)-3-(2-chloro-phenyl)-acryloyl | 4-fluoro-phenyl | 1.50 | E |
| E.71 | (E)-3-(4-chloro-phenyl)-allyl | (E)-3-(2-fluoro-phenyl)-acryloyl | 4-fluoro-phenyl | 1.42 | E |
| E.72 | (E)-3-(4-chloro-phenyl)-allyl | 2-(4-chloro-phenoxy)-acetyl | 4-fluoro-phenyl | 1.42 | E |
| E.73 | (E)-3-(4-chloro-phenyl)-allyl | 2-(2-phenyl-thiazol-4-yl)-acetyl | 4-fluoro-phenyl | 1.50 | E |
| E.74 | (E)-3-(4-chloro-phenyl)-allyl | 4-methylsulfanyl-benozyl | 4-fluoro-phenyl | 1.38 | E |
| E.75 | (E)-3-(4-chloro-phenyl)-allyl | 2,3-dihydro-benzofuran-5-carbonyl | 4-fluoro-phenyl | 1.30 | E |
| E.76 | (E)-3-(4-chloro-phenyl)-allyl | 2-bromo-benzoyl | 4-fluoro-phenyl | 1.40 | E |
| E.77 | (E)-3-(4-chloro-phenyl)-allyl | 2-benzoyl-benzoyl | 4-fluoro-phenyl | 1.44 | E |
| E.78 | (E)-3-(4-chloro-phenyl)-allyl | [1,2,3]thiadiazole-4-carbonyl | 4-fluoro-phenyl | 1.20 | E |
| E.79 | (E)-3-(4-chloro-phenyl)-allyl | thiophene-2-carbonyl | 4-fluoro-phenyl | 1.28 | E |
| E.80 | (E)-3-(4-chloro-phenyl)-allyl | 4-oxo-4H-chromene-2-carbonyl | 4-fluoro-phenyl | 1.30 | E |
| E.81 | (E)-3-(4-chloro-phenyl)-allyl | 4,5,6,7-tetrahydro-benzo[c]thiophene-1-carbonyl | 4-fluoro-phenyl | 1.49 | E |
| E.82 | (E)-3-(4-chloro-phenyl)-allyl | 5-methyl-1-phenyl-1H-pyrazole-4-carbonyl | 4-fluoro-phenyl | 1.30 | E |
| E.83 | (E)-3-(4-chloro-phenyl)-allyl | 3,3,3-trifluoro-propylcarbamoyl | 4-fluoro-phenyl | 1.33 | H |
| E.84 | (E)-3-(4-chloro-phenyl)-allyl | 2-mercapto-ethylcarbamoyl | 4-fluoro-phenyl | 1.40 | H |
| E.85 | (E)-3-(4-chloro-phenyl)-allyl | 2-morpholin-4-yl-ethylcarbamoyl | 4-fluoro-phenyl | 0.80 | H |
| E.86 | (E)-3-(4-chloro-phenyl)-allyl | benzylcarbamoyl | 4-fluoro-phenyl | 1.37 | H |
| E.87 | (E)-3-(4-chloro-phenyl)-allyl | 2-fluoro-benzylcarbamoyl | 4-fluoro-phenyl | 1.39 | H |

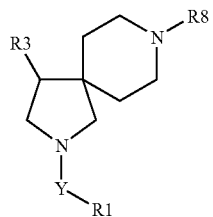

| Compound No | R8 | YR1 | R3 | Retention Time (min) | LC method |
|---|---|---|---|---|---|
| E.88 | (E)-3-(4-chloro-phenyl)-allyl | 1-phenyl-ethylcarbamoyl | 4-fluoro-phenyl | 1.42 | H |
| E.89 | (E)-3-(4-chloro-phenyl)-allyl | 2-phenoxy-ethylcarbamoyl | 4-fluoro-phenyl | 1.41 | H |
| E.90 | (E)-3-(4-chloro-phenyl)-allyl | 3-chloro-benzylcarbamoyl | 4-fluoro-phenyl | 1.46 | H |
| E.91 | (E)-3-(4-chloro-phenyl)-allyl | 4-methoxy-benzylcarbamoyl | 4-fluoro-phenyl | 1.37 | H |
| E.92 | (E)-3-(4-chloro-phenyl)-allyl | 2-trifluoromethoxy-benzylcarbamoyl | 4-fluoro-phenyl | 1.52 | H |
| E.93 | (E)-3-(4-chloro-phenyl)-allyl | 2-trifluoromethyl-benzylcarbamoyl | 4-fluoro-phenyl | 1.50 | H |
| E.94 | (E)-3-(4-chloro-phenyl)-allyl | 4-phenoxy-benzylcarbamoyl | 4-fluoro-phenyl | 1.59 | H |
| E.95 | (E)-3-(4-chloro-phenyl)-allyl | 2-(4-benzyl-piperazin-1-yl)-ethylcarbamoyl | 4-fluoro-phenyl | 1.03 | H |
| E.96 | (E)-3-(4-chloro-phenyl)-allyl | 4-isopropyl-phenylcarbamoyl | 4-fluoro-phenyl | 1.57 | H |
| E.97 | (E)-3-(4-chloro-phenyl)-allyl | o-tolylcarbamoyl | 4-fluoro-phenyl | 1.38 | H |
| E.98 | (6-chloro-naphthalen-2-yl)-methyl | 2-chloro-pyridine-4-carbonyl | 4-fluoro-phenyl | 1.27 | H |
| E.99 | (7-chloro-naphthalen-2-yl)-methyl | 2-chloro-pyridine-4-carbonyl | 4-fluoro-phenyl | 1.26 | H |

The LC methods were as follows
LC-Method A:
ZMD Massenspektrometer from Waters (Single quadrupole mass spectrometer)
Instrument Parameter:
Ionisation method: Electrospray
Polarity: positive ions
Capillary (kV) 3.00, Cone (V) 30.00, Extractor (V) 5.00, Source Temperature (° C.) 120, Desolvation Temperature (° C.) 300, Cone Gas Flow (L/Hr) OFF, Desolvation Gas Flow (L/Hr) 500
Mass range: 150 to 1000 Da
DAD Wavelength range (nm): 200 to 600
HPLC is from Agilent: quarternery HPLC pump HP1100, HP1100 Diodearray Detektor, HP1100 thermostatted column compartment und HP1100 solvent degasser.
A=water with 0.04% HCOOH, B=Acetonitril/Methanol (4:1, v/v)+0.05% HCOOH
Column: YMC-Pack ProC18, 3 micrometer particle size, 120 Angström, 33×3 mm, Temp: 60° C.
The gradient Timetable contains 5 entries which are:

| Time | A % | B % | C % | D % | Flow (ml/min) |
|---|---|---|---|---|---|
| 0.00 | 95.0 | 5.0 | 0.0 | 0.0 | 1.700 |
| 6.00 | 0.0 | 100.0 | 0.0 | 0.0 | 1.700 |
| 7.70 | 0.0 | 100.0 | 0.0 | 0.0 | 1.700 |
| 7.80 | 95.0 | 5.0 | 0.0 | 0.0 | 1.700 |
| 8.20 | 95.0 | 5.0 | 0.0 | 0.0 | 1.700 |

LC-Method B:
ZMD Massenspektrometer from Waters (Single quadrupole mass spectrometer)
Instrument Parameter:
Ionisation method: Electrospray
Polarity: positive ions
Capillary (kV) 3.00, Cone (V) 30.00, Extractor (V) 5.00, Source Temperature (° C.) 120, Desolvation Temperature (° C.) 300, Cone Gas Flow (L/Hr) OFF, Desolvation Gas Flow (L/Hr) 500
Mass range: 150 to 1000 Da
DAD Wavelength range (nm): 200 to 600
HPLC is from Agilent: quarternery HPLC pump HP1100, HP 1100 Diodearray Detektor, HP1100 thermostatted column compartment und HP1100 solvent degasser.
A=water with 0.04% HCOOH, B=Acetonitril/Methanol (4:1, v/v)+0.05% HCOOH
Column: YMC-Pack ProC18, 3 micrometer particle size, 120 Angström, 33×3 mm, Temp: 60° C.

The gradient Timetable contains 5 entries which are:

| Time | A % | B % | C % | D % | Flow (ml/min) |
|---|---|---|---|---|---|
| 0.00 | 95.0 | 5.0 | 0.0 | 0.0 | 1.700 |
| 2.00 | 0.0 | 100.0 | 0.0 | 0.0 | 1.700 |
| 2.80 | 0.0 | 100.0 | 0.0 | 0.0 | 1.700 |
| 2.90 | 95.0 | 5.0 | 0.0 | 0.0 | 1.700 |
| 3.10 | 95.0 | 5.0 | 0.0 | 0.0 | 1.700 |

LC-Method C:
ZQ Massenspektrometer from Waters (Single quadrupole mass spectrometer)
Instrument Parameter:
Ionisation method: Electrospray
Polarity: positive ions
Capillary (kV) 3.00, Cone (V) 30.00, Extractor (V) 5.00, Source Temperature (° C.) 120, Desolvation Temperature (° C.) 300, Cone Gas Flow (L/Hr) OFF, Desolvation Gas Flow (L/Hr) 500
Mass range: 150 to 1000 Da
DAD Wavelength range (nm): 200 to 600
HPLC is from Agilent: quarternery HPLC pump HP1100, HP1100 Diodearray Detektor, HP1100 thermostatted column compartment und HP1100 solvent degasser.
A=water with 0.04% HCOOH, B=Acetonitril/Methanol (4:1, v/v)+0.05% HCOOH
column: YMC-Pack ProC18, 3 micrometer particle size, 120 Angström, 33×3 mm, Temp: 60° C.
The gradient Timetable contains 5 entries which are:

| Time | A % | B % | C % | D % | Flow (ml/min) |
|---|---|---|---|---|---|
| 0.00 | 95.0 | 5.0 | 0.0 | 0.0 | 1.700 |
| 2.00 | 0.0 | 100.0 | 0.0 | 0.0 | 1.700 |
| 2.80 | 0.0 | 100.0 | 0.0 | 0.0 | 1.700 |
| 2.90 | 95.0 | 5.0 | 0.0 | 0.0 | 1.700 |
| 3.10 | 95.0 | 5.0 | 0.0 | 0.0 | 1.700 |

LC-Method D:
ZMD Mass Spectrometer from Waters (Single quadrupole mass spectrometer)
Instrument Parameter:
Ionisation method: Electrospray
Polarity: positive ions
Capillary (kV) 3.80, Cone (V) 30.00, Extractor (V) 3.00, Source Temperature (° C.) 150, Desolvation Temperature (° C.) 350, Cone Gas Flow (L/Hr) OFF, Desolvation Gas Flow (L/Hr) 600
Mass range: 150 to 1000 Da
HPLC is from Agilent: quaternary HPLC pump HP1100, HP1100 Variable Wavelength Detector, HP1100 thermostatted column compartment and HP1100 solvent degasser.
A=water with 0.04% HCOOH, B=Acetonitril/Methanol (4:1, v/v)+0.05% HCOOH
Column: Phenomenex Gemini C18, 3 micrometer particle size, 110 Angström, 30×3 mm, Temp: 60° C.
The gradient Timetable contains 5 entries which are:

| Time | A % | B % | C % | D % | Flow (ml/min) |
|---|---|---|---|---|---|
| 0.00 | 95.0 | 5.0 | 0.0 | 0.0 | 1.700 |
| 2.00 | 0.0 | 100.0 | 0.0 | 0.0 | 1.700 |
| 2.80 | 0.0 | 100.0 | 0.0 | 0.0 | 1.700 |
| 2.90 | 95.0 | 5.0 | 0.0 | 0.0 | 1.700 |
| 3.10 | 95.0 | 5.0 | 0.0 | 0.0 | 1.700 |

LC-Method E:
HPLC: Waters Alliance 2795HT/Waters 996 DAD
MS: Micromass ZMD2000
Column: Waters Atlantis dC18 3ym 3.0×20 mm IS Column
Waters Alliance 2795 LC Mobile Phase

| Solvents | | | |
|---|---|---|---|
| A % | 90.0 | H2O/CH3CN 9:1 HCOOH | 0.1% |
| B % | 10.0 | CH3CN HCOOH | 0.1% |
| C % | 0.0 | H2O/HCOOH | 0.1 |
| D % | 0.0 | H2O/HCOOH | 0.1 |
| Flow Ramp | 2.00 | | |
| Flow (ml/min) | 1.700 | | |
| Stop Time (mins) | 2.90 | | |
| Min Pressure (Bar) | 0 | | |
| Max Pressure (Bar) | 345 | | |
| Degasser OnStroke Volume | 130.0 μl | | |
| Waters Alliance 2795 LC Column | | | |
| Column Position Column 1Equilibration Time (mins) | 0.00 | | |
| Column Temperature (° C.) | 40 | | |
| Column Temperature Limit (° C.) | 20 | | |
| Waters Alliance 2795 LC Rapid Equilibration | | | |
| System Path OffSystem Flow (ml/min) | 2.00 | | |
| System Time (mins) | 2.00 | | |
| Re-equilibration Time (mins) | 0.00 | | |
| Pre column volume (μl) | 0.00 | | |
| Waters Alliance 2795 I/O | | | |
| Switch 1   No ChangeSwitch 2   No ChangeSwitch 3 | | | |
| No ChangeSwitch 4   NoChangeAnalog Output Setting | Flow Rate | | |
| Waters Alliance 2795 LC Gradient Timetable | | | |

The gradient Timetable contains 4 entries which are:

| Time | A % | B % | C % | D % | Flow | Curve |
|---|---|---|---|---|---|---|
| 0.00 | 90.0 | 10.0 | 0.0 | 0.0 | 1.700 | 1 |
| 2.50 | 0.0 | 100.0 | 0.0 | 0.0 | 1.700 | 6 |
| 2.80 | 0.0 | 100.0 | 0.0 | 0.0 | 1.700 | 6 |
| 2.90 | 90.0 | 10.0 | 0.0 | 0.0 | 1.700 | 6 |

LC-Method F:
ZQ Mass Spectrometer from Waters (Single quadrupole mass spectrometer)
Instrument Parameter:
Ionisation method: Electrospray
Polarity: positive ions
Capillary (kV) 3.00, Cone (V) 30.00, Extractor (V) 5.00, Source Temperature (° C.) 150, Desolvation Temperature (° C.) 350, Cone Gas Flow (L/Hr) 50, Desolvation Gas Flow (L/Hr) 500
Mass range: 150 to 1000 Da
DAD Wavelength range (nm): 200 to 500
HPLC is from Agilent: quaternary HPLC pump HP1100, HP1100 Diodearray Detector, HP1100 thermostatted column compartment und HP1100 solvent degasser.
A=water with 0.04% HCOOH, B=Acetonitril/Methanol (4:1, v/v)+0.05% HCOOH
Column: Phenomenex Gemini C18, 3 micrometer particle size, 110 Angström, 30×3 mm, Temp: 60° C.

The gradient Timetable contains 5 entries which are:

| Time | A % | B % | C % | D % | Flow (ml/min) |
|---|---|---|---|---|---|
| 0.00 | 95.0 | 5.0 | 0.0 | 0.0 | 1.700 |
| 2.00 | 0.0 | 100.0 | 0.0 | 0.0 | 1.700 |
| 2.80 | 0.0 | 100.0 | 0.0 | 0.0 | 1.700 |
| 2.90 | 95.0 | 5.0 | 0.0 | 0.0 | 1.700 |
| 3.10 | 95.0 | 5.0 | 0.0 | 0.0 | 1.700 |

LC-Method G:

ZMD Mass Spectrometer from Waters (Single quadrupole mass spectrometer)

Instrument Parameter:

Ionisation method: Electrospray

Polarity: positive ions

Capillary (kV) 3.00, Cone (V) 30.00, Extractor (V) 5.00, Source Temperature (° C.) 120, Desolvation Temperature (° C.) 300, Cone Gas Flow (L/Hr) OFF, Desolvation Gas Flow (L/Hr) 500

Mass range: 150 to 1200 Da

HPLC is from Agilent: quarternery HPLC pump HP1100, HP1100 Variable Wavelength Detector, HP1100 thermostatted column compartment und HP1100 solvent degasser.

A=water with 0.04% HCOOH, B=Acetonitril/Methanol (4:1, v/v)+0.05% HCOOH

Column: YMC-Pack ProC18, 3 micrometer particle size, 120 Angström, 33×3 mm, Temp: 60° C.

The gradient Timetable contains 5 entries which are:

| Time | A % | B % | C % | D % | Flow (ml/min) |
|---|---|---|---|---|---|
| 0.00 | 95.0 | 5.0 | 0.0 | 0.0 | 1.700 |
| 6.00 | 0.0 | 100.0 | 0.0 | 0.0 | 1.700 |
| 7.70 | 0.0 | 100.0 | 0.0 | 0.0 | 1.700 |
| 7.80 | 95.0 | 5.0 | 0.0 | 0.0 | 1.700 |
| 8.20 | 95.0 | 5.0 | 0.0 | 0.0 | 1.700 |

LC-Method H:

HPLC: Agilent 1100 Series

MS: Waters/Micromass ZQ2000

Column: Waters Atlantis dC18 3ym 3.0×20 mm IS Column

HP1100 LC Pump Initial Conditions

| Solvents | |
|---|---|
| A % | 90.0 H2O/CH3CN 9:1 0.1% HCOOH |
| B % | 10.0 CH3CN 0.1% HCOOH |
| C % | 0.0 |
| D % | 0.0 |
| Valve A set to channel | 1 |
| Valve B set to channel | 1 |
| Flow (ml/min) | 1.700 |
| Stop Time (mins) | 3.0 |
| Min Pressure (bar) | 0 |
| Max Pressure (bar) | 400 |
| Oven Temperature Left (° C.) | 40.0 |
| Oven Temperature Right (° C.) | 40.0 |

HP1100 LC Pump Gradient Timetable

The gradient Timetable contains 4 entries which are:

| Time | A % | B % | C % | D % | Flow (ml/min) | Pressure |
|---|---|---|---|---|---|---|
| 0.00 | 90.0 | 10.0 | 0.0 | 0.0 | 1.700 | 400 |
| 2.50 | 0.0 | 100.0 | 0.0 | 0.0 | 1.700 | 400 |
| 2.80 | 0.0 | 100.0 | 0.0 | 0.0 | 1.700 | 400 |
| 2.90 | 90.0 | 10.0 | 0.0 | 0.0 | 1.700 | 400 |

EXAMPLE 2

This Example illustrates the pesticidal/insecticidal properties of compounds of formula (I). Test against were performed as follows:

Spodoptera littoralis (Egyptian Cotton Leafworm)

Cotton leaf discs were placed on agar in a 24-well microtiter plate and sprayed with test solutions at an application rate of 200 ppm. After drying, the leaf discs were infested with 5 $L_1$ larvae. The samples were checked for mortality, repellent effect, feeding behaviour, and growth regulation 3 days after treatment (DAT). The following compounds gave at least 80% control of Spodoptera littoralis: E.2, E.3, E.4, E.5, E.7, E.8, E.9, E.10, E.21, E.22, E.23, E.24, E.26, E.33, E.37, E.44, E.47, E.48, E.59, E.62, E.68 and E.98.

Heliothis virescens (Tobacco Budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of Heliothis virescen: E.1, E.2, E.3, E.5, E.7, E.9, E.22, E.23, E.25, E.26 and E.98.

Plutella xylostella (Diamond Back Moth):

24-well microtiter plate (MTP) with artificial diet was treated with test solutions at an application rate of 18.2 ppm by pipetting. After drying, the MTP's were infested with larvae (L2) (10-15 per well). After an incubation period of 5 days, samples were checked for larval mortality, antifeedant and growth regulation. The following compounds gave at least 80% control of Plutella xylostella: E.1, E.2, E.3, E.5, E.7, E.8, E.9, E.16, E.22, E.23, E.24, E.35, E.52, E.53, E.60 and E.94.

Diabrotica balteata (Corn Root Worm):

A 24-well microtiter plate (MTP) with artificial diet was treated with test solutions at an application rate of 200 ppm (concentration in well 18 ppm) by pipetting. After drying, the MTP's were infested with larvae (L2) (6-10 per well). After an incubation period of 5 days, samples were checked for larval mortality, and growth regulation. The following compounds gave at least 80% control of Diabrotica balteata: E.1, E.2, E.3, E.4, E.5, E.7, E.9, E.21, E.23, E.44, E.83 and E.91.

Aedes aegypti (Yellow Fever Mosquito):

10-15 Aedes larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of Aedes aegypti: E.2, E.3, E.4, E.5, E.7, E.9, E.10, E.17, E.18, E.21, E.22, E.23, E.24, E.25, E.26, E.32, E.37, E.38, E.39, E.43, E.44, E.46, E.47 and E.98.

The invention claimed is:

1. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

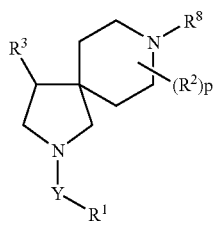

(I)

wherein
Y is C=O, C=S or S(O)$_m$;
m is 0, 1 or 2;
$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$;
$R^{13}$ and $R^{14}$ are each independently hydrogen, $COR^{15}$, optionally substituted alkyl, optionally substituted aryl, optionally substituted heteroaryl, or optionally substituted heterocyclyl;
or $R^{13}$ and $R^{14}$ together with the N atom to which they are attached form a group —N=C($R^{16}$)—$NR^{17}R^{18}$;
or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups;
$R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$;
$R^{16}$, $R^{17}$ and $R^{18}$ are each independently H or lower alkyl;
$R^{19}$ and $R^{20}$ are independently optionally substituted alkyl, optionally substituted aryl or optionally substituted heteroaryl;
$R^3$ is a benzene, pyridine, or thiophene ring substituted by 0, 1, 2 or 3 $R^4$ groups;
each $R^4$ group is independently halogen, $C_{1-8}$ haloalkyl, $C_{1-8}$ alkoxy or $C_{1-6}$ haloalkoxy;
$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;
each $R^2$ is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$;
$R^{23}$ and $R^{24}$ are, each independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, or $C_{1-6}$ alkoxycarbonyl;
or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two $R^2$ groups attached to the same carbon atom are =O, =S, =$NR^5$, =$CR^6R^7$;
$R^5$, $R^6$ and $R^7$ are each independently H or optionally substituted alkyl; and
p is 0, 1, 2, 3 or 4; or salts or N-oxides thereof.

2. A method according to claim 1 wherein Y is C=O or C=S.

3. A method according to claim 1 wherein
$R^1$ is hydrogen, $C_{1-6}$ alkyl, $C_{1-6}$ cyanoalkyl, $C_{1-6}$ haloalkyl, $C_{3-7}$ cycloalkyl($C_{1-4}$) alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$) alkyl (wherein the aryl group may be optionally substituted by halo, nitro, cyano, $C_{1-6}$ alkyl, $C_{1-6}$haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, haloalkylthio or $NR^{13}R^{14}$; and $R^{13}$ and $R^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl), phenyl ($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl ($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino)).

4. A method according to claim 1 wherein $R^2$ is independently halo, cyano, $C_{1-3}$ alkyl, or hydroxy, or two $R^2$ groups together with the carbon atom to which they are attached form $=O$, $=S$, $=NR^5$, or $=CR^6R^7$;

$R^5$, $R^6$ and $R^7$ are each independently H or optionally substituted alkyl; and p is 0, 1 or 2.

5. A method according to claim 1 wherein $R^3$ is a 6-membered aromatic ring or is 5 or 6 membered heteroaromatic ring wherein the ring members are each independently CH, S, N, $NR^4$, O, or $CR^4$ provided that there are no more than one O or S atoms present in the ring;

each $R^4$ is independently halogen, cyano, $C_{1-8}$ alkyl, $C_{1-8}$ haloalkyl, $C_{1-6}$ cyanoalkyl, $C_{1-6}$ alkoxy($C_{1-6}$)alkyl, $C_{3-7}$ cycloalkyl($C_{1-6}$)alkyl, $C_{5-6}$ cycloalkenyl($C_{1-6}$)alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, trimethylsilyl($C_{2-6}$)alkynyl, aminocarbonyl($C_{2-6}$)alkynyl, $C_{1-6}$ alkylaminocarbonyl($C_{2-6}$)alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), or heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy);

or 2 adjacent groups $R^4$ together with the atoms to which they are attached form a 4, 5, 6 or 7 membered carbocyclic, heteroaromatic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^9R^{10}$ N; and $R^9$ and $R^{10}$ are each independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, or $C_{1-6}$ alkoxycarbonyl;

or $R^9$ and $R^{10}$ together with the N atom to which they are attached form a five, six or seven-membered heterocyclic ring which may contain one or two further heteroatoms selected from O, N or S and which may be optionally substituted by one or two $C_{1-6}$ alkyl groups.

6. A method according to claim 1 wherein $R^8$ is $C_{1-10}$ alkyl, $C_{1-10}$ haloalkyl, aryl($C_{1-6}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$) alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or —C($R^{51}$)($R^{52}$)—[$CR^{53}$=$CR^{54}$]z-$R^{55}$;

z is 1 or 2;

$R^{51}$ and $R^{52}$ are each independently H, halo or $C_{1-2}$ alkyl;

$R^{53}$ and $R^{54}$ are each independently H, halogen, $C_{1-4}$ alkyl or $C_{1-4}$ haloalkyl; and $R^{55}$ is optionally substituted aryl or optionally substituted heteroaryl.

7. A compound of formula I'

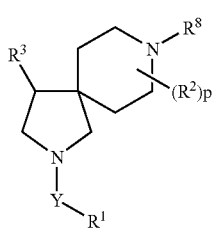

(I')

wherein

Y is C=O, C=S or $S(O)_m$ where m is 0, 1 or 2;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$;

$R^{13}$ and $R^{14}$ are each independently hydrogen, $COR^{15}$, optionally substituted alkyl, optionally substituted aryl, optionally substituted heteroaryl, or optionally substituted heterocyclyl;

or $R^{13}$ and $R^{14}$ together with the N atom to which they are attached form a group —N=C($R^{16}$)—$NR^{17}R^{18}$;

or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups;

$R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$;

$R^{16}$, $R^{17}$ and $R^{18}$ are each independently H or lower alkyl;

$R^{19}$ and $R^{20}$ are each independently optionally substituted alkyl, optionally substituted aryl or optionally substituted heteroaryl;

$R^3$ is optionally substituted aryl or optionally substituted heteroaryl;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

each $R^2$ is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$;

$R^{23}$ and $R^{24}$ are each independently hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, or $C_{1-6}$ alkoxycarbonyl;

or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two $R^2$ groups attached to the same carbon atom are =O, =S, =$NR^5$, =$CR^6R^7$;

$R^5$, $R^6$ and $R^7$ are each independently H or optionally substituted alkyl; and p is 0, 1, 2, 3 or 4;

or salts or N-oxides thereof; provided $R^3$ is not unsubstituted phenyl.

8. A compound of formula

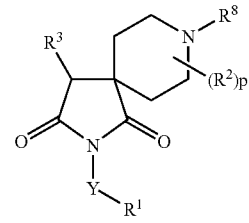

wherein

Y is C=O, C=S or $S(O)_m$ where m is 0, 1 or 2;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$;

$R^{13}$ and $R^{14}$ are each independently hydrogen, $COR^{15}$, optionally substituted alkyl, optionally substituted aryl, optionally substituted heteroaryl, or optionally substituted heterocyclyl;

or $R^{13}$ and $R^{14}$ together with the N atom to which they are attached form a group —N=C($R^{16}$)—$NR^{17}R^{18}$;

or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups;

$R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$;

$R^{16}$, $R^{17}$ and $R^{18}$ are each independently H or lower alkyl;

$R^{19}$ and $R^{20}$ are independently optionally substituted alkyl, optionally substituted aryl or optionally substituted heteroaryl;

$R^3$ is optionally substituted aryl or optionally substituted heteroaryl;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

each $R^2$ is independently halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$;

$R^{23}$ and $R^{24}$ are each independently hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, or $C_{1-6}$ alkoxycarbonyl;

or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two $R^2$ groups attached to the same carbon atom are =O, =S, =$NR^5$, =$CR^6R^7$;

$R^5$, $R^6$ and $R^7$ are each independently H or optionally substituted alkyl; and p is 0, 1, 2, 3 or 4;

or salts or N-oxides thereof; provided $R^3$ is not unsubstituted phenyl.

9. An insecticidal, acaricidal or nematicidal composition comprising an insecticidally, acaricidally or nematicidally effective amount of a compound of formula I as defined in claim 1.

10. An insecticidal, acaricidal or nematicidal composition according to claim 9 further comprising a surface active agent and an inert diluents or carrier.

11. An insecticidal, acaricidal or nematicidal composition according to claim 9 further comprising a fertilizer.

12. A method according to claim 1 wherein Y is C=O, C=S or S(O)$_m$ where m is 0, 1 or 2.

13. A compound according to claim 7 wherein $R^3$ is a benzene, pyridine, or thiophene ring substituted by 0, 1, 2 or 3 $R^4$ groups; and each $R^4$ group is independently halogen, $C_{1-8}$ haloalkyl, $C_{1-8}$ alkoxy or $C_{1-6}$ haloalkoxy.

14. A compound according to claim 7 wherein $R^1$ is hydrogen, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$;

$R^{13}$ and $R^{14}$ are each independently $COR^{15}$, optionally substituted aryl, optionally substituted heteroaryl, or optionally substituted heterocyclyl;

or $R^{13}$ and $R^{14}$ together with the N atom to which they are attached form a group —N=C($R^{16}$)—$NR^{17}R^{18}$;

or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups;

$R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$;

$R^{16}$, $R^{17}$ and $R^{18}$ are each independently H or lower alkyl; and $R^{19}$ and $R^{20}$ are independently optionally substituted alkyl, optionally substituted aryl or optionally substituted heteroaryl.

15. An insecticidal, acaricidal or nematicidal composition comprising an insecticidally, acaricidally or nematicidally effective amount of a compound of claim 7.

16. An insecticidal, acaricidal or nematicidal composition comprising an insecticidally, acaricidally or nematicidally effective amount of a compound of claim 14.

17. A compound according to claim 8 wherein $R^3$ is a benzene, pyridine, or thiophene ring substituted by 0, 1, 2 or 3 $R^4$ groups; and each $R^4$ group is independently halogen, $C_{1-8}$ haloalkyl, $C_{1-8}$ alkoxy or $C_{1-6}$ haloalkoxy.

18. A compound according to claim 8 wherein $R^1$ is hydrogen, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$;

$R^{13}$ and $R^{14}$ are each independently $COR^{15}$, optionally substituted aryl, optionally substituted heteroaryl, or optionally substituted heterocyclyl;

or $R^{13}$ and $R^{14}$ together with the N atom to which they are attached form a group —N=C($R^{16}$)—$NR^{17}R^{18}$;

or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups;

$R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$;

$R^{16}$, $R^{17}$ and $R^{18}$ are each independently H or lower alkyl; and $R^{19}$ and $R^{20}$ are independently optionally substituted alkyl, optionally substituted aryl or optionally substituted heteroaryl.

19. An insecticidal, acaricidal or nematicidal composition comprising an insecticidally, acaricidally or nematicidally effective amount of a compound of claim 8.

20. An insecticidal, acaricidal or nematicidal composition comprising an insecticidally, acaricidally or nematicidally effective amount of a compound of claim 18.

* * * * *